US011007508B2

(12) United States Patent
Kauffman et al.

(10) Patent No.: US 11,007,508 B2
(45) Date of Patent: May 18, 2021

(54) PHENOL ALKYLATION CATALYST PRECURSOR AND CATALYST, METHOD OF FORMING CATALYST, METHOD OF REGENERATING CATALYST, AND METHOD OF ALKYLATING PHENOL

(71) Applicant: SABIC Global Technologies B.V., Bergen op Zoom (NL)

(72) Inventors: James Kauffman, Katy, TX (US); Gary Mell Bates, Voorheesville, NY (US); Douglas Henry Lenz, Troy, NY (US); Kenchaiah Lohith, Bangalore (IN); Vivek Chandra Gyani, Bangalore (IN); Omoyemen E. Ofoegbu, Sugar Land, TX (US); Robin Woodbury, Sugar Land, TX (US); Xin Li, Sugar Land, TX (US); Xiankuan Zhang, Houston, TX (US)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 200 days.

(21) Appl. No.: 16/321,247

(22) PCT Filed: Jul. 28, 2017

(86) PCT No.: PCT/US2017/044411
§ 371 (c)(1),
(2) Date: Jan. 28, 2019

(87) PCT Pub. No.: WO2018/023015
PCT Pub. Date: Feb. 1, 2018

(65) Prior Publication Data
US 2019/0176132 A1 Jun. 13, 2019

Related U.S. Application Data

(60) Provisional application No. 62/368,232, filed on Jul. 29, 2016.

(51) Int. Cl.
*B01J 23/78* (2006.01)
*B01J 37/08* (2006.01)
(Continued)

(52) U.S. Cl.
CPC ............... *B01J 23/78* (2013.01); *B01J 21/18* (2013.01); *B01J 23/02* (2013.01); *B01J 23/94* (2013.01);
(Continued)

(58) Field of Classification Search
CPC ... B01J 21/16; B01J 23/02; B01J 23/72; B01J 23/78; B01J 23/94; B01J 27/28;
(Continued)

(56) References Cited

U.S. PATENT DOCUMENTS 3,764,630 A * 10/1973 Van Sorge .............. C07C 39/06
568/804
3,833,673 A * 9/1974 Brannock ............... C07C 39/07
568/716
(Continued)

FOREIGN PATENT DOCUMENTS

AU 484413 4/1975
EP 0127833 12/1984
(Continued)

OTHER PUBLICATIONS

International Search Report for International Application No. PCt/US2017/044411 filed on Jul. 28, 2017; dated Sep. 21, 2018; 9 pages.
(Continued)

Primary Examiner — Patricia L. Hailey
(74) Attorney, Agent, or Firm — Cantor Colburn LLP

(57) ABSTRACT

A phenol alkylation catalyst exhibiting a desirable combination of activity, selectivity, and regenerability is prepared from a catalyst precursor that includes specific amounts of magnesium oxide, copper oxide or a copper oxide precursor,
(Continued)

a hydrous magnesium aluminosilicate-containing binder, a pore-former, a lubricant, and water. Methods of forming and regenerating the catalyst, as well as a phenol alkylation method, are described.

11 Claims, 5 Drawing Sheets

(51) Int. Cl.

| | |
|---|---|
| *B01J 23/94* | (2006.01) |
| *B01J 37/00* | (2006.01) |
| *B01J 35/10* | (2006.01) |
| *B01J 38/14* | (2006.01) |
| *B01J 37/04* | (2006.01) |
| *B01J 35/02* | (2006.01) |
| *C07C 37/14* | (2006.01) |
| *B01J 38/16* | (2006.01) |
| *C07C 39/06* | (2006.01) |
| *B01J 35/00* | (2006.01) |
| *B01J 38/20* | (2006.01) |
| *B01J 21/18* | (2006.01) |
| *B01J 23/02* | (2006.01) |
| *B01J 31/04* | (2006.01) |
| *B01J 31/28* | (2006.01) |
| *B01J 37/12* | (2006.01) |
| *B01J 38/02* | (2006.01) |
| *C07C 37/11* | (2006.01) |
| *B01J 37/18* | (2006.01) |

(52) U.S. Cl.
CPC .............. *B01J 31/04* (2013.01); *B01J 31/28* (2013.01); *B01J 35/0026* (2013.01); *B01J 35/023* (2013.01); *B01J 35/1004* (2013.01); *B01J 35/1014* (2013.01); *B01J 35/1019* (2013.01); *B01J 35/1038* (2013.01); *B01J 35/1066* (2013.01); *B01J 37/0009* (2013.01); *B01J 37/0018* (2013.01); *B01J 37/0063* (2013.01); *B01J 37/04* (2013.01); *B01J 37/084* (2013.01); *B01J 37/086* (2013.01); *B01J 37/088* (2013.01); *B01J 37/12* (2013.01); *B01J 38/02* (2013.01); *B01J 38/14* (2013.01); *B01J 38/16* (2013.01); *B01J 38/20* (2013.01); *C07C 37/11* (2013.01); *C07C 37/14* (2013.01); *C07C 39/06* (2013.01); *B01J 37/18* (2013.01); *C01P 2006/10* (2013.01); *C01P 2006/11* (2013.01); *C01P 2006/12* (2013.01); *Y02P 20/584* (2015.11)

(58) Field of Classification Search
CPC ........ B01J 31/04; B01J 31/28; B01J 35/0026; B01J 35/023; B01J 35/1004; B01J 35/1014; B01J 35/1019; B01J 35/1038; B01J 35/1066; B01J 37/0009; B01J 37/0018; B01J 37/0063; B01J 37/04; B01J 37/084; B01J 37/086; B01J 37/088; B01J 37/12; B01J 37/18; B01J 38/02; B01J 38/14; B01J 38/16; B01J 38/20; C07C 37/11; C07C 37/14; C07C 39/06; Y02P 20/584; C01P 2006/10; C01P 2006/11; C01P 2006/12
USPC .................................... 502/20, 34, 340, 345
See application file for complete search history.

(56) References Cited

U.S. PATENT DOCUMENTS

| | | | | |
|---|---|---|---|---|
| 3,873,628 | A | * | 3/1975 | Van Sorge .............. C07C 37/16 568/804 |
| 3,962,126 | A | * | 6/1976 | Pecak ...................... B01J 21/20 502/22 |
| 4,217,244 | A | | 8/1980 | Montgomery |
| 4,375,566 | A | * | 3/1983 | Kawamata ............ C07C 37/055 568/716 |
| 4,554,266 | A | * | 11/1985 | Bennett .................... B01J 23/72 502/340 |
| 4,590,307 | A | * | 5/1986 | Bennett, Jr. .............. B01J 23/34 502/174 |
| 4,851,591 | A | * | 7/1989 | Battista .................... B01J 21/10 568/804 |
| 4,933,509 | A | * | 6/1990 | Warner .................... C07C 37/16 568/804 |
| 5,432,146 | A | * | 7/1995 | Winston ................. A01N 59/04 504/101 |
| 5,847,237 | A | | 12/1998 | Yago et al. |
| 6,261,987 | B1 | * | 7/2001 | Watson .................... B01J 21/10 502/183 |
| 6,291,724 | B1 | | 9/2001 | Braat |
| 6,620,908 | B2 | | 9/2003 | Watson et al. |
| 6,897,175 | B2 | | 5/2005 | Parrillo et al. |
| 7,081,432 | B2 | | 7/2006 | Ingelbrecht et al. |
| 7,208,438 | B2 | | 4/2007 | Ingelbrecht et al. |
| 7,288,683 | B2 | | 10/2007 | Ingelbrecht et al. |
| 2005/0009697 | A1 | * | 1/2005 | Ingelbrecht ............. C07C 37/16 502/340 |
| 2005/0075237 | A1 | | 4/2005 | Kelly et al. |
| 2012/0157294 | A1 | * | 6/2012 | Ruettinger ........... B01J 37/0009 502/73 |

FOREIGN PATENT DOCUMENTS

| | | | | |
|---|---|---|---|---|
| EP | 0129065 | | 12/1984 | |
| WO | 2005097721 | | 10/2005 | |
| WO | 2014046696 | | 3/2014 | |
| WO | 2018/060811 | * | 4/2018 | ............. C07C 37/16 |

OTHER PUBLICATIONS

Written Opinion of the International Searching Authority for International Application No. PCt/US2017/044411 filed on Jul. 28, 2017; dated Sep. 21; 2018; 14 pages.

* cited by examiner

PHENOL ALKYLATION CATALYST PRECURSOR AND CATALYST, METHOD OF FORMING CATALYST, METHOD OF REGENERATING CATALYST, AND METHOD OF ALKYLATING PHENOL

BACKGROUND OF THE INVENTION

Alkylation of phenol with an alkanol to form a 2,6-dialkylphenol is a well-established industrial process. For example, phenol can be alkylated with methanol to form 2,6-dimethylphenol (also known as 2,6-xylenol), which is a monomer used to form the thermoplastic poly(2,6-dimethyl-1,4-phenylene ether). Alkylation catalysts containing magnesium oxide are commonly employed and often generated by calcination of catalyst precursor containing magnesium carbonate. See, e.g., U.S. Pat. No. 6,620,908 B2 to Watson et al, issued 16 Sep. 2003; U.S. Pat. No. 6,897,175 B2 to Parrillo et al., issued 24 May 2005; and U.S. Pat. No. 7,081,432 to Ingelbrecht et al., issued 25 Jul. 2006. Catalysts prepared by this method can exhibit high catalytic activity and selectivity for 2,6-alkylation. However, they often exhibit poor structural integrity that is manifested as a fracturing of catalyst particles to create fines, a pressure drop across the catalyst bed (decreasing productivity), a limited useful lifetime (requiring frequent catalyst replacement and associated process downtime), and an inability to be regenerated and reused. There is therefore a need for magnesium oxide-based alkylation catalysts that exhibit improved structural integrity while maintaining catalyst activity and selectivity.

BRIEF SUMMARY OF EMBODIMENTS OF THE INVENTION

One embodiment is a catalyst precursor comprising, based on the total weight of the catalyst precursor: 70 to 98 weight percent magnesium oxide; 0.1 to 2 weight percent copper oxide or a copper oxide precursor; 0.5 to 8 weight percent a binder comprising a hydrous magnesium aluminosilicate; 1 to 15 weight percent a pore-former; 0.2 to 5 weight percent a lubricant; and 0.2 to 15 weight percent water.

Another embodiment is a method of forming a phenol alkylation catalyst, the method comprising: exposing the catalyst precursor in any of its variations to a nitrogen gas flow having a weight hourly space velocity of 0.05 to 0.8 hour$^{-1}$, wherein the nitrogen gas flow has a temperature of 350 to 550° C. and is conducted for a time of 5 to 30 hours, and wherein the temperature of the nitrogen gas flow is increased to the temperature of 350 to 550° C. at a rate of 0.5 to 5° C./minute.

Another embodiment is a method of regenerating a phenol alkylation catalyst, the method comprising: exposing the phenol alkylation catalyst to a first gas flow having a weight hourly space velocity of 0.05 to 0.8 hour$^{-1}$, a temperature of 410 to 440° C., and a pressure of 25 to 400 kilopascals, wherein the gas flow comprises nitrogen; and exposing the phenol alkylation catalyst to a second gas flow having a weight hourly space velocity of 0.05 to 0.8 hour$^{-1}$, a temperature of 10 to 50° C. greater than the temperature of the first gas flow, and a pressure of 25 to 400 kilopascals, wherein the gas flow comprises nitrogen.

Another embodiment is a method of alkylating phenol, the method comprising: reacting phenol with a $C_1$-$C_6$ alkanol in the presence of the phenol alkylation catalyst in any of its variations.

These and other embodiments are described in detail below.

DETAILED DESCRIPTION OF THE INVENTION

Figure 1:
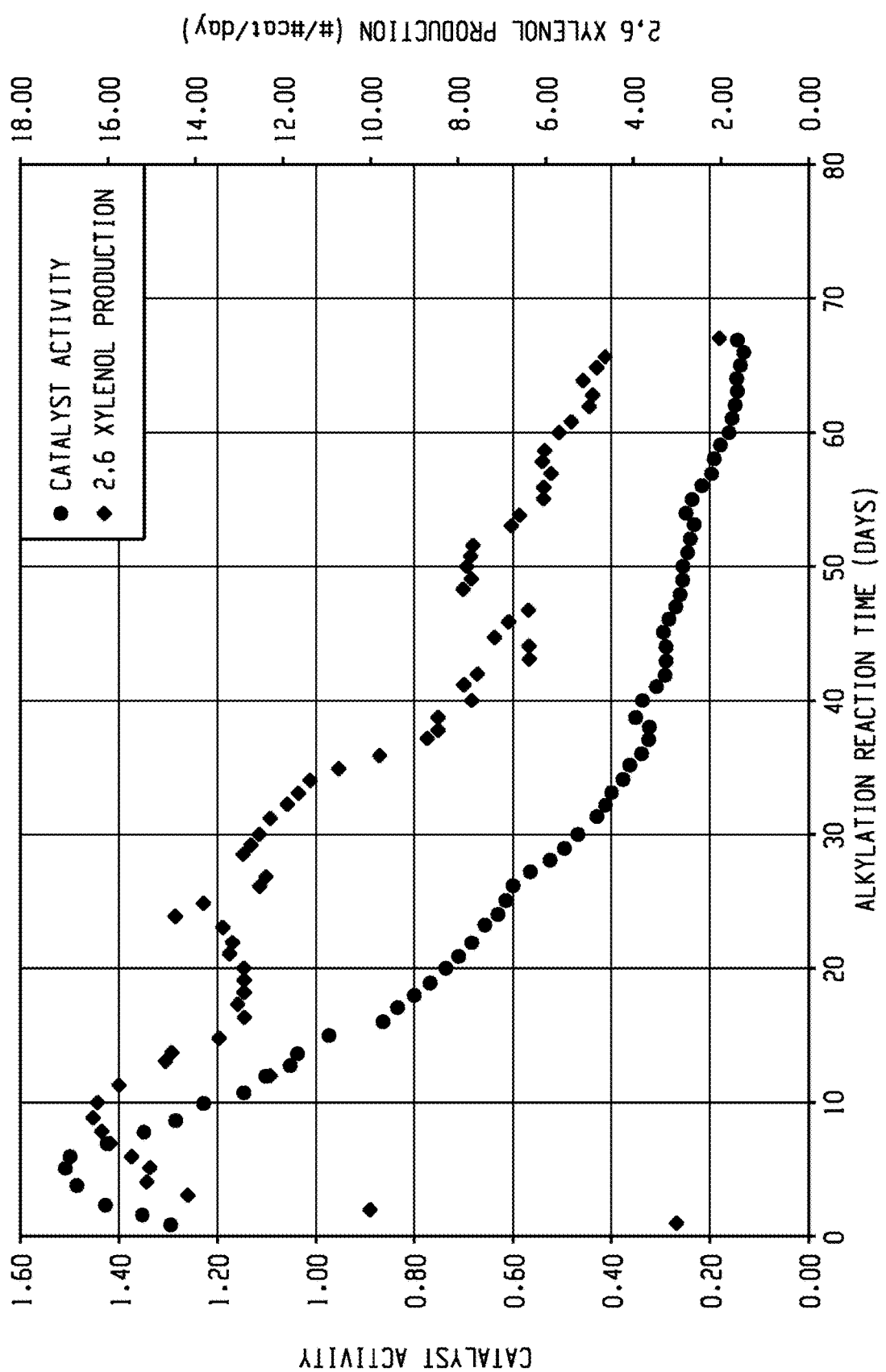
FIG. 1 is a plot of catalyst activity (which is unitless; blue dots) and 2,6-xylenol productivity (in kilograms 2,6-xylenol per kilogram catalyst per day; red diamonds) as a function of time in a commercial scale reactor for a comparative catalyst that does not have the structural integrity to tolerate regeneration.

The present inventors have determined that a particular catalyst precursor composition allows for the formation of magnesium oxide-based alkylation catalysts that exhibit improved structural integrity relative to comparative catalysts, while maintaining catalyst activity and selectivity. The improved structural integrity of the alkylation catalyst makes it possible for it to be regenerated without physically disintegrating, as observed for the comparative catalyst. The regeneration of the catalyst, in turn, provides increased productivity of alkylated phenol for a given reactor.

One embodiment is a catalyst precursor comprising, based on the total weight of the catalyst precursor: 70 to 98 weight percent magnesium oxide; 0.1 to 2 weight percent copper oxide or a copper oxide precursor; 0.5 to 8 weight percent a binder comprising a hydrous magnesium aluminosilicate; 1 to 15 weight percent a pore-former; 0.2 to 5 weight percent a lubricant; and 0.2 to 15 weight percent water.

The catalyst precursor comprises magnesium oxide (MgO). In some embodiments, the magnesium oxide has a Brunauer-Emmett-Teller (BET) surface area of at least 70 meter$^2$/gram. Within this limit, the magnesium oxide surface area can be 70 to 500 meter$^2$/gram, or 100 to 500 meter$^2$/gram, or 150 to 500 meter$^2$/gram, or 100 to 200 meter$^2$/gram. BET surface areas were determined on a Micromeritics ASAP 2010 instrument. The samples were thoroughly degassed at 300° C. for 5 hours under vacuum to remove water and other physically adsorbed species. The measurements were made using nitrogen gas as the adsorbent at 77 K and a multipoint method of calculation was used for determining surface area of the catalyst. Pore volume, expressed in units of centimeter$^3$/gram, was determined at relative pressure $P/P_0=0.99$, and average pore diameter, expressed in units of Angstroms, was calculated using the formula $10^{-4}(V)/(BET\ SA)$, where "V" is the pore volume in units of centimeter$^3$/gram, and "BET SA" is the BET surface area in units of meter$^2$/gram.

In some embodiments, the magnesium oxide has an aspect ratio of less than or equal to 3:1, or 1.1:1 to 3:1, or 1.2:1 to 2.5:1, or 1.3:1 to 2:1. Aspect ratio is defined as the number average ratio of the largest particle dimension to the smallest orthogonal dimension of the same particle. Aspect ratio can be determined by laser diffraction.

The catalyst precursor comprises the magnesium oxide in an amount of 70 to 98 weight percent, based on the total weight of the catalyst precursor. Within this range, the magnesium oxide amount can be 75 to 95 weight percent, or 78 to 90 weight percent.

In addition to the magnesium oxide, the catalyst precursor comprises copper oxide or a copper oxide precursor. As used herein, copper oxide refers to cupric oxide (CuO). In some embodiments, the copper oxide or a copper oxide precursor comprises cupric oxide, cupric nitrate, cuprous carbonate, a hydrate of one of the foregoing, or a combination thereof.

The catalyst precursor comprises the copper oxide or copper oxide precursor in an amount of 0.1 to 2 weight percent, based on the total weight of the catalyst precursor. Within this range, the copper oxide or copper oxide precursor amount can be 0.2 to 1 weight percent, or 0.3 to 0.8 weight percent.

In addition to the magnesium oxide and the copper oxide or copper oxide precursor, the catalyst precursor comprises a binder comprising a hydrous magnesium aluminosilicate. Hydrous magnesium aluminosilicate are naturally occurring materials, and they are commercially available at various levels of purification. Examples of purified hydrous magnesium aluminosilicates include MIN-U-GEL™ 200, MIN-U-GEL™ 400, MIN-U-GEL™ 500, MIN-U-GEL™ PC, and MIN-U-GEL™ FG, all available from ActiveMinerals International LLC. An example of a highly purified hydrous magnesium aluminosilicate is ACTI-GEL™ 208, available from ActiveMinerals International LLC. In some embodiments, the hydrous magnesium aluminosilicate comprises a hydrated or hydroxylated magnesium aluminosilicate.

The catalyst precursor comprises the hydrous magnesium aluminosilicate in an amount of 0.5 to 8 weight percent, based on the total weight of the catalyst precursor. Within this range, the hydrous magnesium aluminosilicate amount can be 1 to 6 weight percent, or 1.5 to 5.5 weight percent.

In addition to the magnesium oxide, the copper oxide or copper oxide precursor, and the hydrous magnesium aluminosilicate, the catalyst precursor comprises a pore-former. As used herein, the term pore former refers a substance capable of aiding the formation of pores in the calcined catalyst (i.e., the product of calcining the catalyst precursor). Pore formers include paraffin wax, polyethylene wax, microcrystalline wax, montan wax, cellulose, carboxyl methyl cellulose, cellulose acetate, starch, walnut powder, citric acid, polyethylene glycol, oxalic acid, stearic acid, $C_{10}$-$C_{28}$ anionic surfactants (including those with neutralized carboxylic acid, phosphoric acid, and sulfonic acid groups), $C_{10}$-$C_{28}$ cationic surfactants (including those with ammonium and phosphonium groups), and combinations thereof. In some embodiments, the pore former comprises a polyethylene glycol.

The catalyst precursor comprises the pore-former in an amount of 1 to 15 weight percent, based on the total weight of the catalyst precursor. Within this range, the pore former amount can be 2 to 10 weight percent.

In addition to the magnesium oxide, the copper oxide or copper oxide precursor, the hydrous magnesium aluminosilicate, and the pore-former, the catalyst precursor comprises a lubricant. Suitable lubricants include graphite, $C_8$-$C_{24}$ carboxylic acids (including octanoic acid, decanoic acid, dodecanoic acid, tetradecanoic acid, hexadecanoic acid, octadecanoic acid (stearic acid), eicosanic acid, docosanoic acid, tetracosanoic acid, magnesium salts of the $C_8$-$C_{24}$ carboxylic acids, talcs, silicas, waxes, glycerol, starches, and combinations thereof. In some embodiments, the lubricant comprises magnesium stearate.

The catalyst precursor comprises the lubricant in an amount of 0.2 to 5 weight percent, based on the total weight of the catalyst precursor. Within this range, the lubricant amount can be 0.4 to 3.5 weight percent, or 0.6 to 2.5 weight percent.

In addition to the magnesium oxide, the copper oxide or copper oxide precursor, the hydrous magnesium aluminosilicate, the pore-former, and the lubricant, the catalyst precursor comprises water. In some embodiments, the water is deionized. The catalyst precursor comprises the water in an amount of 0.2 to 15 weight percent, based on the total weight of the catalyst precursor. Within this range, the water amount can be 0.6 to 12 weight percent.

Procedures for forming the catalyst precursor composition, and for shaping it into pellets, are provided in the working examples below. In some embodiments, the catalyst precursor has a density of 1.2 to 2 grams per milliliter, or 1.3 to 1.8 grams per milliliter, at 23° C. In this context, density refers to the unpacked density of catalyst precursor pellets, determined as described in the working examples.

In a very specific embodiment of the catalyst precursor, it comprises 75 to 95 weight percent of the magnesium oxide; 0.2 to 1 weight percent of the copper oxide or copper oxide precursor; 1 to 6 weight percent of the binder comprising a hydrous magnesium aluminosilicate; 2 to 10 weight percent of the pore-former; 0.4 to 3.5 weight percent of the lubricant; and 0.6 to 12 weight percent of the water.

Another embodiment is a method of forming a phenol alkylation catalyst, the method comprising: exposing the catalyst precursor in any of its above-described variations to a nitrogen gas flow having a weight hourly space velocity of 0.05 to 0.8 hour$^{-1}$, or 0.1 to 0.4 hour$^1$, wherein the nitrogen gas flow has a temperature of 350 to 550° C., or 400 to 500° C., and is conducted for a time of 5 to 30 hours, or 8 to 24 hours, and wherein the temperature of the nitrogen gas flow is increased to the temperature of 350 to 550° C. at a rate of 0.5 to 5° C./minute, or 1 to 4° C./minute. This method of forming a phenol alkylation catalyst can also be called a method of calcining the catalyst precursor.

In some embodiments, the freshly calcined phenol alkylation catalyst exhibits a crush strength of 1 to 20 Newtons/millimeter, or 5 to 20 Newtons/millimeter, determined according to ASTM D4179-11, "Standard Test Method for Single Pellet Crush Strength of Formed Catalysts and Catalyst Carriers".

Another embodiment is a method of regenerating a phenol alkylation catalyst, the method comprising: exposing the phenol alkylation catalyst to a first gas flow having a weight hourly space velocity of 0.05 to 0.8 hour$^{-1}$, a temperature of 410 to 440° C., and a pressure of 25 to 400 kilopascals, wherein the gas flow comprises nitrogen; and exposing the phenol alkylation catalyst to a second gas flow having a weight hourly space velocity of 0.05 to 0.8 hour$^{-1}$, a temperature of 10 to 50° C. greater than the temperature of the first gas flow, and a pressure of 25 to 400 kilopascals, wherein the gas flow comprises nitrogen.

Thus, the method includes at least two regeneration steps. In the first step, within the range of 0.05 to 0.8 hour$^{-1}$, the weight hourly space velocity can be 0.1 to 0.4 hour$^{-1}$; within the range of 410 to 440° C., the temperature can be 415 to 435° C.; within the range of 25 to 400 kilopascals, the pressure can be 50 to 200 kilopascals; and the gas flow can comprise 75 to 97 mole percent nitrogen and 3 to 25 mole percent oxygen, or 80 to 95 mole percent nitrogen and 5 to 20 mole percent oxygen. In the second step, within the range of 0.05 to 0.8 hour$^{-1}$, the weight hourly space velocity can be 0.1 to 0.4 hour$^{-1}$; within the temperature difference of 10 to 50° C., the temperature of the second gas flow can be 15 to 45° C. greater than the temperature of the first gas flow; and the second gas flow can comprise 75 to 97 mole percent nitrogen and 3 to 25 mole percent oxygen, or 80 to 95 mole percent oxygen. In some embodiments, the duration of each step is specified not as a particular number of hours, but in terms of oxygen breakthrough in the reactor effluent. For example, the process can be transitions from first step conditions to second step conditions when the oxygen content of the effluent reaches 25% of the oxygen content of the feed. In some embodiments, the gas flow (feed) in each step comprises less than or equal to 1 mole percent water, or no water.

Another embodiment is a method of alkylating phenol, the method comprising: reacting phenol with a $C_1$-$C_6$ alkanol in the presence of the phenol alkylation catalyst in any of its variations. In some embodiments, the $C_1$-$C_6$ alkanol comprises methanol.

In a very specific embodiment of the method of alkylating phenol, the $C_1$-$C_6$ alkanol comprises methanol, reacting phenol with the $C_1$-$C_6$ alkanol is characterized by a feed weight hourly space velocity of 0.5 to 10 hour$^{-1}$ or 1 to 5 hour$^{-1}$, a pressure of 50 to 500 kilopascals or 80 to 350 kilopascals, a molar ratio of $C_1$-$C_6$ alkanol to phenol of 2:1 to 10:1 or 3:1 to 9:1, and a temperature of 450 to 490° C. or 455 to 480° C.

The invention includes at least the following embodiments.

Embodiment 1

A catalyst precursor comprising, based on the total weight of the catalyst precursor: 70 to 98 weight percent magnesium oxide; 0.1 to 2 weight percent copper oxide or a copper oxide precursor; 0.5 to 8 weight percent a binder comprising a hydrous magnesium aluminosilicate; 1 to 15 weight percent a pore-former; 0.2 to 5 weight percent a lubricant; and 0.2 to 15 weight percent water.

Embodiment 2

The catalyst precursor of embodiment 1, having a density of 1.2 to 2 grams per milliliter at 23° C., determined as described in the working examples.

Embodiment 3

The catalyst precursor of embodiment 1 or 2, wherein the magnesium oxide has a Brunauer-Emmett-Teller surface area of at least 70 meter$^2$/gram.

Embodiment 4

The catalyst precursor of any one of embodiments 1-3, wherein the copper oxide or a copper oxide precursor comprises cupric oxide, cupric nitrate, cuprous carbonate, a hydrate of one of the foregoing, or a combination thereof.

Embodiment 5

The catalyst precursor of any one of embodiments 1-4, wherein the pore-former comprises polyethylene glycol.

Embodiment 6

The catalyst precursor of any one of embodiments 1-5, wherein the lubricant comprises graphite, magnesium stearate, or a combination thereof.

Embodiment 7

The catalyst precursor of any one of embodiments 1-6, comprising 75 to 95 weight percent of the magnesium oxide; 0.2 to 1 weight percent of the copper oxide or copper oxide precursor; 1 to 6 weight percent of the binder comprising a hydrous magnesium aluminosilicate; 2 to 10 weight percent of the pore-former; 0.4 to 3.5 weight percent of the lubricant; and 0.6 to 12 weight percent of the water.

Embodiment 8

A method of forming a phenol alkylation catalyst, the method comprising: exposing the catalyst precursor of any one of embodiment 1-7 to a nitrogen gas flow having a weight hourly space velocity of 0.05 to 0.8 hour$^{-1}$, wherein the nitrogen gas flow has a temperature of 350 to 550° C. and is conducted for a time of 5 to 30 hours, and wherein the temperature of the nitrogen gas flow is increased to the temperature of 350 to 550° C. at a rate of 0.5 to 5° C./minute.

Embodiment 9

A phenol alkylation catalyst prepared by the method of embodiment 8.

Embodiment 10

The phenol alkylation catalyst of embodiment 9, exhibiting a crush strength of 1 to 20 Newtons/millimeter, determined according to ASTM D4179-11.

Embodiment 11

A method of alkylating phenol, the method comprising: reacting phenol with a $C_1$-$C_6$ alkanol in the presence of the phenol alkylation catalyst of embodiment 9 or 10.

Embodiment 12

The method of embodiment 12, wherein the $C_1$-$C_6$ alkanol comprises methanol, said reacting phenol with a $C_1$-$C_6$ alkanol is characterized by a feed weight hourly space velocity of 0.5 to 10 hour$^{-1}$, a pressure of 50 to 500 kilopascals, a molar ratio of $C_1$-$C_6$ alkanol to phenol of 2:1 to 10:1, and a temperature of 450 to 490° C.

Embodiment 13

A method of regenerating a phenol alkylation catalyst, the method comprising: exposing the phenol alkylation catalyst to a first gas flow having a weight hourly space velocity of 0.05 to 0.8 hour$^{-1}$, a temperature of 410 to 440° C., and a pressure of 25 to 400 kilopascals, wherein the gas flow comprises nitrogen; exposing the phenol alkylation catalyst to a second gas flow having a weight hourly space velocity of 0.05 to 0.8 hour$^{-1}$, a temperature of 10 to 50° C. greater than the temperature of the first gas flow, and a pressure of 25 to 400 kilopascals, wherein the gas flow comprises nitrogen.

All ranges disclosed herein are inclusive of the endpoints, and the endpoints are independently combinable with each other. Each range disclosed herein constitutes a disclosure of any point or sub-range lying within the disclosed range.

The invention is further illustrated by the following non-limiting examples.

EXAMPLES

The following components were used to form catalyst precursors.

TABLE 1

| Component | Description |
| --- | --- |
| Water | Water, CAS Reg. No. 7732-18-5, having a purity of at least 99.9%, was obtained as deionized water. |
| $Cu(NO_3)_2 \cdot 3H_2O$ | Copper (II) nitrate trihydrate, CAS Reg. No. 10031-43-3, having a purity of at least 99.5%, was obtained from Strem Chemicals. |
| MgO | Magnesium oxide, CAS Reg. No. 1309-48-4, having a purity of at least 93%, was obtained from Dead Sea Periclase Ltd. |
| Graphite | Graphite, CAS Reg. No. 7782-42-5, nominally 100% pure, was obtained as graphite from Asbury Carbon. |
| MgSt | Magnesium stearate, CAS Reg. No. 557-04-0; obtained as Synpro Mg Stearate 90C from Valerus Specialty Chemicals, or as magnesium stearate technical grade from SigmaAldrich. |
| PEG | Polyethylene glycol, CAS Reg. No. 25322-68-3, having a nominal purity of 100% and a number average molecular weight of 400 grams/mole, was obtained from Spectrum Fine Chemicals. |
| HPMAS | (Highly Purified Magnesium Aluminosilicate) Hydrous magnesium aluminosilicate, CAS Reg. No. 12174-11-7, having a purity of about 93 to 95 weight percent, obtained as ACTI-GEL ™ 208 from ActiveMinerals International LLC. |
| PMAS | (Purified Magnesium Aluminosilicate) Hydrous magnesium aluminosilicate, CAS Reg. No. 8031-18-3, having a purity of greater than 90 weight percent, obtained as MIN-U-GEL ™ 200, MIN-U-GEL ™ 400, or MIN-U-GEL ™ MB from ActiveMinerals International LLC. |
| Phenol | Phenol, CAS Reg. No. 108-95-2, having a purity of at least 90 percent; obtained from Fisher Scientific. |
| Methanol | Methanol, CAS Reg. No. 67-56-1, having a purity of at least 99.8 percent; obtained from Sigma-Aldrich. |

Comparative Example 1

This example describes the preparation of a comparative alkylation catalyst. A bag dump station is used to load catalyst components into a ribbon blender. The material is discharged through a slide gate and rotary valve (to regulate flow) to a horizontal screw conveyor. The screw conveyor discharges into the lower feed hopper of a FitzMill™ comminution hammer mill connected to a Chilsonator™ dry granulation roller compactor, which densifies and granulates the blended catalyst powder. The screw conveyor is run at a constant speed as the feed to the system is controlled by the rotary valve. A bucket elevator is used to convey material to the upper feed hopper. The material is then processed through the densification & granulation system, screened to approximately −16+36 mesh (U.S. Standard), recycling the oversize and fines back to the compactor using the same bucket elevator. The screened feed product is discharged through a pneumatic conveying system to a surge tank, and then conveyed a second time to the tablet press systems. The tableting process pelletizes these feed particles to produce pellets that were 0.190 inch (4.76 millimeter) in diameter and 0.140 inch (3.56 millimeters) long. The final pellets have a density of 1.60 grams/centimeter$^3$, and a crush strength of 31.0 Newtons/millimeter, determined according to ASTM D4179-11. These catalyst precursor pellets, which have not been calcined, are sometimes referred to as "green pellets".

Example 1

Catalyst Precursor Preparation. In 10 milliliters (mL) of water, 0.74 grams (g) of copper (II) nitrate trihydrate was dissolved. The copper solution was added dropwise to 100 g of magnesium oxide and thoroughly mixed. To the mixture was added 2 g of graphite, 10 g of polyethylene glycol, and 2 g of HPMAS. The mixture was mixed thoroughly to ensure homogeneity. Using a 2.54 centimeter (1 inch) diameter Carver press die, the mix was pressed into 2.54 centimeter (1 inch) diameter tablets at a pressing pressure of 34.5 megapascals (5000 pounds per square inch (psi)). The average density of the resulting tablets was about 1 g/mL. The tablets were ground and sized to a mesh size of −20+40 mesh, corresponding to nominal sieve openings of 400 to 841 micrometers. The sized particles were fed into the hopper of a single die press. Using a die size of 4.76 millimeters (3/16 inch), the sized particles were made into 4.76 millimeter (3/16 inch) diameter pellets. The settings on the tablet press were adjusted to obtain pellets of density in the range 1.4 to 1.7 g/mL. The pellets were ground and sized to a mesh size of −20+40 mesh (400 to 841 micrometers) and used as the catalyst precursor.

Conversion of Catalyst Precursor to Catalyst. The catalyst precursor was converted to catalyst by continuously flowing nitrogen at a rate of 30 milliliters/minute (mL/min) through the stainless steel reactor having an outer diameter of 1.27 centimeters (0.5 inch), a wall thickness of 1.24 millimeters (0.049 inch), and a length of 43.2 centimeters (17 inches). The reactor contained 5 grams of the catalyst precursor held in the mid-section of the reactor by silicon carbide and quartz wool. The nitrogen was pre-heated by passing through a vaporizer maintained at a temperature of 200° C. The reactor temperature was ramped from room temperature (23° C.) to 393° C. at a rate of 2° C./min and held for 15.5 hours at that temperature. It was then ramped to 450° C. at a rate of 2° C./min, and held for 1.5 hours, then reduced to 440° C., at which temperature it was used for the alkylation described below.

Alkylation. Following the activation step, the nitrogen flow was stopped and a feed mixture of 12.36 mole percent (mole %) phenol, 49.46 mole % methanol, and 38.17 mole % water was introduced into the vaporizer at a flowrate of 3.5 milliliters/hour (mL/hr), and then to the reactor. The reactor temperature was maintained at 440° C. for 12 hours. The feed flowrate was increased to 13.8 mL/hr and the reactor temperature was increased to 460° C. and held for 24 hrs. Finally the feed flowrate was maintained at 13.8 mL/hr while the reactor temperature was increased to 470° C. and held until the end of the test. The total time on stream was about 100 hours. Throughout the run, effluent gas samples were analyzed by an in-line gas chromatograph (GC). Table 2 summarizes alkylation performance data from the reaction.

Example 2

Catalyst Precursor Preparation. In 5 mL of water, 0.74 g of copper (II) nitrate trihydrate was dissolved. The copper solution was added dropwise to 100 g of magnesium oxide and thoroughly mixed. To the mixture was added 2 g of graphite, 5 g of polyethylene glycol, and 2 g of HPMAS. The mixture was mixed thoroughly to ensure homogeneity. Using a 2.54 centimeter (1 inch) diameter Carver press die, the mix was pressed into 2.54 centimeter (1 inch) diameter tablets at a pressing pressure of 34.5 megapascals (5000 pounds per square inch (psi)). The average density of the resulting tablets was about 1 g/mL. The tablets were ground and sized to a mesh size of −20+40 mesh, corresponding to nominal sieve openings of 400 to 841 micrometers. The sized particles were fed into the hopper of a single die press. Using a die size of 4.76 millimeters (3/16 inch), the sized particles were made into 4.76 millimeter (3/16 inch) diameter pellets. The settings on the tablet press were adjusted to obtain pellets of density in the range 1.4 to 1.7 g/mL. The pellets were ground and sized to a mesh size of −20+40 mesh (400 to 841 micrometers) and used as the catalyst precursor.

The conversion and alkylation procedures of Example 1 were repeated.

Example 3

Catalyst Precursor Preparation. In 2.5 mL of water, 0.35 g of copper (II) nitrate trihydrate was dissolved. The copper solution was added dropwise to 50 g of magnesium oxide and thoroughly mixed. To the mixture was added 1 g of graphite, 2.5 g of polyethylene glycol, and 2.5 g of HPMAS. The mixture was mixed thoroughly to ensure homogeneity. Using a 2.54 centimeter (1 inch) diameter Carver press die, the mix was pressed into 2.54 centimeter (1 inch) diameter tablets at a pressing pressure of 34.5 megapascals (5000 pounds per square inch (psi)). The average density of the resulting tablets was about 1 g/mL. The tablets were ground and] sized to a mesh size of −20+40 mesh, corresponding to nominal sieve openings of 400 to 841 micrometers. The sized particles were fed into the hopper of a single die press. Using a die size of 4.76 millimeters (3/16 inch), the sized particles were made into 4.76 millimeter (3/16 inch) diameter pellets. The settings on the tablet press were adjusted to obtain pellets of density in the range 1.4 to 1.7 g/mL. The pellets were ground and sized to a mesh size of −20+40 mesh (400 to 841 micrometers) and used as the catalyst precursor.

The conversion and alkylation procedures of Example 1 were repeated.

Example 4

Catalyst Precursor Preparation. In 0.5 mL of water, 0.35 g of copper (II) nitrate trihydrate was dissolved. The copper solution was added dropwise to 50 g of magnesium oxide and thoroughly mixed. To the mixture was added 1 g of graphite, 2.5 g of polyethylene glycol, and 2.5 g of HMAS 2. The mixture was mixed thoroughly to ensure homogeneity.

Using a 2.54 centimeter (1 inch) diameter Carver press die, the mix was pressed into 2.54 centimeter (1 inch) diameter tablets at a pressing pressure of 34.5 megapascals (5000 pounds per square inch (psi)). The average density of the resulting tablets was about 1 g/mL. The tablets were ground and sized to a mesh size of −20+40 mesh, corresponding to nominal sieve openings of 400 to 841 micrometers. The sized particles were fed into the hopper of a single die press. Using a die size of 4.76 millimeters (3/16 inch), the sized particles were made into 4.76 millimeter (3/16 inch) diameter pellets. The settings on the tablet press were adjusted to obtain pellets of density in the range 1.4 to 1.7 g/mL. The pellets were ground and sized to a mesh size of −20+40 mesh (400 to 841 micrometers) and used as the catalyst precursor.

The conversion and alkylation procedures of Example 1 were repeated.

Example 5

Catalyst Precursor Preparation. A mixture of 50 g of magnesium oxide, 1 g of graphite, 2.5 g of polyethylene glycol, and 2.5 g of HPMAS was prepared. To the mixture, 5 mL of water was added dropwise and mixed thoroughly. Using a 2.54 centimeter (1 inch) diameter Carver press die, the mix was pressed into 2.54 centimeter (1 inch) diameter tablets at a pressing pressure of 103.4 megapascals (15,000 pounds per square inch (psi)). The average density of the resulting tablets was about 1.5 g/mL. The tablets were ground and sized to a mesh size of −20+40 mesh, corresponding to nominal sieve openings of 400 to 841 micrometers. Copper was added to the sized particles via incipient wetting. This was done by dissolving 0.054 g of copper (II) nitrate trihydrate in 6.27 g of ethanol, and adding it dropwise to the sized particles. The wetted particles were dried in a muffle oven at 80° C. for about 16 hrs. The dried particles were used as the catalyst precursor.

The conversion and alkylation procedures of Example 1 were repeated.

Example 6

Catalyst Precursor Preparation. To 100 g of magnesium oxide, 5 g of PEG, 5 g of HMAS, 0.44 g of copper (II) carbonate basic ($Cu_2CO_3(OH)_2$) and 1 g of magnesium stearate were added and thoroughly mixed. To the resulting powder mix, 5 mL of water was added dropwise and dispersed by mixing. The powder mixture was pressed into 4.76 millimeters (3/16 inch) pellets using a die press. The pellets were used as the catalyst precursor.

Conversion of Catalyst Precursor to Catalyst. The catalyst precursor was activated by continuously flowing nitrogen at a rate of 40 milliliters/minute through a stainless steel reactor having an outer diameter of 1.91 centimeter (¾ inch), a wall thickness of 1.24 millimeters (0.049 inch), and a length of 60.96 centimeters (24 inches). The reactor contained 10 g of the catalyst precursor held in the mid-section of the tube by silicon carbide and quartz wool. The nitrogen was pre-heated by passing through a vaporizer maintained at a temperature of 200° C. The reactor temperature was ramped from 23° C. to 393° C. at a rate of 2° C./minute and held for 15.5 hours at that temperature. It was then ramped to 450° C. at a rate of 2° C./min, and held for 1.5 hours before the temperature was reduced to 440° C., at which temperature it was used for the alkylation described below.

Alkylation. Following the activation step, the nitrogen flow was stopped, and a mixture of 5 mole percent hydrogen and 95 mole percent nitrogen was flowed through the catalyst at 40 mL/min for 3 hours, then the reactor was purged with nitrogen at 40 mL/min for about 15 minutes. Following the nitrogen purge, a feed mixture of 12.36 mole percent phenol, 49.46 mole percent methanol, and 38.17 mole percent water, was introduced into the vaporizer at a flowrate of 7.5 mL/hr, and then to the reactor. The reactor temperature was maintained at 440° C. for 12 hours. The feed flowrate was increased to 29.5 mL/hr and the reactor temperature was increased to 460° C. and held for 24 hours. Finally the feed flowrate was maintained at 29.5 mL/hr while the reactor temperature was increased to 470° C. and held until the end of the test. The total time on stream was about 100 hrs. Throughout the run, liquid effluent samples were collected and analyzed by in-line GC.

Table 2 summarizes catalyst properties and alkylation performance. In Table 2, "Green Pellet" refers to pellets of catalyst precursor prior to calcination. "Green Pellet density (g/mL)" is measured as follows. Green pellets are poured into a tared 500 mL graduated cylinder to a volume of 500 mL. The cylinder is not tapped or otherwise agitated to induce denser packing of the pellets. The pellet-filed cylinder is weighed on a METTLER PB1502-S scale, and the weight of the unpacked pellets is calculated by subtracting the tare weight from the weight of the pellet-filled cylinder. The "untapped" density is calculated by dividing the weight of the unpacked pellets, in grams, by 500 milliliters.

In Table 2, "Green Crush Strength (N/mm)" is determined on 10 pellets from each side of the press (20 pellets total), one at a time, using a PHARMATRON™ 8 M Tablet Hardness Tester. Results from the 20 tests are averaged to provide the value in Table 2, where "TOS" is the time on-stream, which includes the alkylation time, but not any regeneration time; "Avg. Phenol Conversion btw TOS of 40-60 hrs (%)" is it 100 times the moles of any phenol conversion product divided by moles of phenol introduced to the reactor; "Total 2,6-xylenol prod. @ ~TOS of 60 hrs" is the moles of 2,6-xylenol divided by the moles of converted phenol between 40 and 60 hours on-stream; "Avg. ortho-selectivity btw TOS of 40-60 hrs" is the sum of the moles of 2,6-xylenol and the moles of ortho-cresol, divided by the moles of converted phenol between 40 and 60 hours on-stream. Table 2 demonstrates that the catalyst of this invention has improved structural integrity—even after multiple regenerations—compared to the comparative catalyst. This improved structural integrity allows the inventive catalyst to be regenerated, which in turn results in greater 2,6-xylenol productivity for a given reactor.

The importance of the surface area and pore size distribution data for the calcined catalyst is because the higher the surface area and pore size, the higher the catalyst activity. Relating the surface area and pore size distribution of the green catalyst tablets to the final calcined tablets surface area and pore size distribution allows prediction from the green tablets how the calcined tablets are going to perform in the reactor.

The reactor testing to produce these results involves loading 10 to 20 grams of catalyst precursor into a 12.7 to 25.4 millimeters (0.5 to 1 inch) inner diameter reactor tube. The catalyst is calcined according to the calcination protocol described in this application and then the phenol/methanol/water feed is fed to the reactor through the catalyst bed to produce, primarily, 2,6-xylenol and ortho-cresol. Because coke develops on the catalyst over time it blocks the magnesium oxide surface from the reactants and the catalyst activity drops. Once the catalyst activity drops below an acceptable level then the reaction is stopped and regeneration of the catalyst is carried out as described to burn off the coke and allow the catalyst activity to increase back to about the original activity level.

TABLE 2

|  | Green Pellet Density (g/mL) | Green Crush Strength (N/mm) | Avg. Phenol Conversion btw TOS of 40-60 hrs (%) | Total 2,6-xylenol prod. @ ~TOS of 60 hrs | Total mesitol prod. @ ~TOS of 60 hrs | Avg. 2,6-xylenol selectivity btw TOS of 40-60 hrs | Avg. ortho-selectivity btw TOS of 40-60 hrs |
|---|---|---|---|---|---|---|---|
| Ex. 1 | 1.65 | 29.4 | 70.1 | 8.9 | 2.8 | 20.9 | 88.0 |
| Ex. 2 | 1.69 | 32.4 | 75.2 | 15.5 | 3.0 | 40.5 | 82.9 |
| Ex. 3 | 1.70 | 33.7 | 89.6 | 25.2 | 4.4 | 68.0 | 93.7 |
| Ex. 4 | 1.67 | 41.3 | 67.8 | 12.8 | 2.5 | 34.4 | 91.6 |
| Ex. 5 | 1.52 | — | 81.8 | 14.2 | 2.7 | 40.5 | 95.1 |
| Ex. 6 | 1.24 | 6.2 | 82.3 | 25.7 | 3.5 | 60.0 | 94.1 |
| C. Ex. 1 | 1.60 | 31.0 | 84.9 | 20.0 | 2.9 | 58.0 | 91.7 |

Examples 7 and 8

Five (5) grams of green pellets were placed in the center of a quartz glass tube. Quartz wool placed on both ends of the catalyst bed was used to maintain the position of the bed in the tube. The tube was placed in a CARBOLITE™ furnace. The upstream end of the tube was connected to house nitrogen and air supplies via plastic tubing. Mass flow controllers were used to regulate the flow rate of the house gases. The upstream end of the tube was also connected to an ISCO™ pump which supplied water during calcination via a stainless steel tube. The exit end of the stainless steel tube was positioned within the furnace inside the quartz wool. This was done to ensure the water is vaporized prior to contacting the pellets. The downstream end of the quartz tube was connected to a moisture trap to collect every liquid exiting the tube. The furnace containing the quartz tube was inclined to aid the flow of liquid out of the tube and prevent back flow. The temperature profile was set on the CARBOLITE™ furnace temperature controller. The furnace temperature was allowed to reach 200° C. before the ISCO pump was turned on. Also, the pump was turned off before the furnace went below 200° C. Green pellets made with either graphite or magnesium stearate lubricants and 0.25% copper (for complete formulations of the Example 7 and 8 compositions, see Table 3, where component amounts are expressed in parts by weight) were calcined by heating at a rate of 2° C./min to the calcination temperature of 390° C. in air at a weight hourly space velocity (WHSV) of 0.2 hr$^{-1}$, steam at a WHSV of 0.0 hr$^{-1}$, and atmospheric pressure. The catalyst was held at this calcination temperature for 12 hours. The effect of calcination conditions was determined by the percent loss of pellet density, percent loss of pellet crush strength, percent loss in surface area, percent decrease in pore volume, and percent increase in average pore diameter of the calcined pellets compared with the green pellets. Minimizing these changes is preferred. Table 4 summarizes properties of the green pellets, and Table 5 summarizes properties of the calcined pellets relative to the green pellets. In Table 4, "Green Pellet Copper (%)" is the weight percent of copper based on the total weight of the catalyst precursor, as determined by x-ray fluorescence. "Green Pellet Surface Area (m$^2$/g)" (the catalyst precursor surface area, in meter$^2$/gram), "Green Pellet Total Pore Volume (cm$^3$/g)" (the catalyst precursor pore volume, in centimeter$^3$/gram), and "Green Pellet Average Pore Diameter (Å)" (the catalyst precursor average pore diameter, in Angstroms), were all determined by BET methods as described above.

TABLE 3

| Component | Example 7 | Example 8 |
|---|---|---|
| MgO | 85.5 | 85.5 |
| PEG | 4.3 | 4.3 |
| HPMAS | 4.3 | 4.3 |
| Water | 4.3 | 4.3 |
| Cu(NO$_3$)$_2$•3H$_2$O | 0.9 | 0.9 |
| Graphite | 0.9 | 0.0 |
| MgSt | 0.0 | 0.9 |

TABLE 4

| | Lubricant | Green Pellet Copper (%) | Green Pellet Density (g/cm$^3$) | Green Pellet Crush Strength (N/mm) | Green Pellet Surface Area (m$^2$/g) | Green Pellet Total Pore Volume (cm$^3$/g) | Green Pellet Average Pore Diameter (Å) |
|---|---|---|---|---|---|---|---|
| Ex. 7 | graphite | 0.25 | 1.63 | 4.8 | 118 | 0.35 | 120 |
| Ex. 8 | MgSt | 0.25 | 1.51 | 2.9 | 94 | 0.38 | 162 |

TABLE 5

| | Lubricant | Calcined Pellet Copper (%) | Calcined Pellet Density Loss (%) | Calcined Pellet Crush Strength Loss (%) | Calcined Pellet Surface Area Loss (%) | Calcined Pellet Total Pore Volume Loss (%) | Calcined Pellet Average Pore Diameter Increase (%) |
|---|---|---|---|---|---|---|---|
| Ex. 7 | graphite | 0.25 | 15.34 | 59.58 | 30.33 | 22.86 | 11.67 |
| Ex. 8 | MgSt | 0.25 | 12.58 | 36.73 | 6.92 | 2.37 | 4.75 |

Examples 9 and 10

The same system and method for calcination were used as described for Examples 7 and 8. Green pellets made with either graphite or magnesium stearate lubricants and 0.4% copper (for complete formulations of the Example 9 and 10 compositions, see Table 6, where component amounts are expressed in weight percent based on the total weight of the composition) were calcined by heating at the rate of 2° C./minute to the calcination temperature of 425° C. in nitrogen at a WHSV of 0.2 hr$^{-1}$, steam at a WHSV of 0.0 hr$^{-1}$, and atmospheric pressure. The catalyst was held at this calcination temperature for 4 hours. The effect of calcination conditions was determined as described for Examples 7 and 8. The initial green pellet properties and the calcination results are summarized in Table 7 and 8, respectively.

TABLE 6

| Component | Example 9 | Example 10 |
|---|---|---|
| MgO | 85.1 | 85.1 |
| PEG | 4.3 | 4.3 |
| HPMAS | 4.3 | 4.3 |
| Water | 4.3 | 4.3 |
| Cu(NO$_3$)$_2$•3H$_2$O | 1.3 | 1.3 |
| Graphite | 0.9 | 0.0 |
| MgSt | 0.0 | 0.9 |

TABLE 7

| | Lubricant | Green Pellet Copper (%) | Green Pellet Density (g/cm$^3$) | Green Pellet Crush Strength (N/mm) | Green Pellet Surface Area (m$^2$/g) | Green Pellet Total Pore Volume (cm$^3$/g) | Green Pellet Average Pore Diameter (Å) |
|---|---|---|---|---|---|---|---|
| Ex. 9 | graphite | 0.40 | 1.56 | 3.6 | 114 | 0.47 | 165 |
| Ex. 10 | MgSt | 0.40 | 1.49 | 3.2 | 93 | 0.37 | 159 |

TABLE 8

| | Lubricant | Calcined Pellet Copper (%) | Calcined Pellet Density Loss (%) | Calcined Pellet Crush Strength Loss (%) | Calcined Pellet Surface Area Loss (%) | Calcined Pellet Total Pore Volume Loss (%) | Calcined Pellet Average Pore Diameter Increase (%) |
|---|---|---|---|---|---|---|---|
| Ex. 9 | graphite | 0.40 | 9.62 | 36.59 | 29.95 | 42.55 | −15.36 |
| Ex. 10 | MgSt | 0.40 | 12.75 | 36.59 | 12.67 | −3.78 | 18.67 |

Examples 11 and 12

The same system and method for calcination was used as described for Examples 7 and 8. Green pellets made with either graphite or magnesium stearate lubricants and 0.4% copper. The catalyst precursor compositions for Examples 11 and 12 are the same as those for Examples 9 and 10, respectively (see Table 6). Catalyst precursor pellets were calcined by heating at the rate of 2° C./min to the calcination temperature of 390° C. in air at a WHSV of 0.5 hr$^{-1}$, steam at a WHSV of 0.0 hr$^{-1}$, and atmospheric pressure. The catalyst was held at this calcination temperature for 4 hours. The effect of calcination conditions was determined as described for Examples 7 and 8. The initial green pellet properties for Examples 11 and 12 are the same as those for Examples 9 and 10, respectively (see Table 7). Properties of the calcined catalysts relative to the respective catalyst precursors are summarized in Table 9.

TABLE 9

| | Lubricant | Calcined Pellet Copper (%) | Calcined Pellet Density Loss (%) | Calcined Pellet Crush Strength Loss (%) | Calcined Pellet Surface Area Loss (%) | Calcined Pellet Total Pore Volume Loss (%) | Calcined Pellet Average Pore Diameter Increase (%) |
|---|---|---|---|---|---|---|---|
| Ex. 11 | graphite | 0.40 | 9.62 | 47.49 | 23.82 | 36.17 | −15.36 |
| Ex. 12 | MgSt | 0.40 | 10.74 | 35.65 | 19.59 | −4.05 | 29.35 |

Examples 13 and 14

The same system and method for calcination was used as described for Examples 7 and 8. Green pellets made with either graphite or magnesium stearate lubricants and 0.4% copper. The Example 13 and 14 compositions are the same as those of Examples 9 and 10, respectively (see Table 6). Catalyst precursor pellets were calcined by heating at a rate of 0.4° C./min to the calcination temperature of 425° C. in nitrogen at a WHSV of 0.5 hr$^{-1}$, steam at a WHSV of 0.16 hr$^{-1}$, and atmospheric pressure. The catalyst was held at this calcination temperature for 4 hours. The effect of calcination conditions was determined as described for Examples 7 and 8. The initial green pellet properties for Examples 13 and 14 are the same as those for Examples 9 and 10, respectively (see Table 7). Properties of the calcined catalysts relative to the respective catalyst precursors are summarized in Table 10.

TABLE 10

| | Lubricant | Calcined Pellet Copper (%) | Calcined Pellet Density Loss (%) | Calcined Pellet Crush Strength Loss (%) | Calcined Pellet Surface Area Loss (%) | Calcined Pellet Total Pore Volume Loss (%) | Calcined Pellet Average Pore Diameter Increase (%) |
|---|---|---|---|---|---|---|---|
| Ex. 13 | graphite | 0.40 | 9.62 | 55.87 | 37.65 | 17.02 | 32.16 |
| Ex. 14 | MgSt | 0.40 | 9.40 | 38.17 | 17.58 | 4.65 | 15.58 |

Examples 15 and 16

The same system and method for calcination was used as described for Examples 7 and 8. Green pellets made with either graphite or magnesium stearate lubricants and 0.4% copper. The Example 15 and 16 compositions are the same as those for Examples 9 and 10 (see Table 6). Catalyst precursor tablets were calcined by heating at a rate of 2.0° C./min to the calcination temperature of 390° C. in nitrogen at a WHSV of 0.2 hr$^{-1}$, steam at a WHSV of 0.16 hr$^{-1}$, and atmospheric pressure. The catalyst was held at this calcination temperature for 12 hours. The effect of calcination conditions was determined as described for Examples 7 and 8. The initial green pellet properties for Examples 15 and 16 are the same as those for Examples 9 and 10, respectively (see Table 7). Properties of the calcined catalysts relative to the respective catalyst precursors are summarized in Table 11.

TABLE 11

| | Lubricant | Calcined Pellet Copper (%) | Calcined Pellet Density Loss (%) | Calcined Pellet Crush Strength Loss (%) | Calcined Pellet Surface Area Loss (%) | Calcined Pellet Total Pore Volume Loss (%) | Calcined Pellet Average Pore Diameter Increase (%) |
|---|---|---|---|---|---|---|---|
| Ex. 15 | graphite | 0.40 | 10.45 | 53.63 | 34.59 | 17.02 | 26.78 |
| Ex. 16 | MgSt | 0.40 | 13.42 | 46.69 | 20.63 | −0.54 | 26.44 |

Examples 17 and 18

The same system and method for calcination was used as described for Examples 7 and 8. Green pellets made with either graphite or magnesium stearate lubricants and 0.25% copper. The compositions of Examples 17 and 18 are the same as those of Examples 7 and 8 (see Table 3). Catalyst precursor pellets were calcined by heating at a rate of 0.4° C./min to the calcination temperature of 425° C. in air at a WHSV of 0.5 hr$^{-1}$, steam at a WHSV of 0.0 hr$^{-1}$, and atmospheric pressure. The catalyst was held at this calcination temperature for 4 hours. The effect of calcination conditions was determined as described for Examples 7 and 8. The initial green pellet properties for Examples 17 and 18 are the same as those for Examples 7 and 8, respectively (see Table 4). Properties of the calcined catalysts relative to the respective catalyst precursors are summarized in Table 12.

TABLE 12

| | Lubricant | Calcined Pellet Copper (%) | Calcined Pellet Density Loss (%) | Calcined Pellet Crush Strength Loss (%) | Calcined Pellet Surface Area Loss (%) | Calcined Pellet Total Pore Volume Loss (%) | Calcined Pellet Average Pore Diameter Increase (%) |
|---|---|---|---|---|---|---|---|
| Ex. 17 | graphite | 0.25 | 12.88 | 66.74 | 37.61 | −5.89 | 68.25 |
| Ex. 18 | MgSt | 0.25 | 10.60 | 28.23 | 25.62 | 8.95 | 22.37 |

Examples 19 and 20

The same system and method for calcination was used as described for Examples 7 and 8. Green pellets made with either graphite or magnesium stearate lubricants and 0.25% copper. The compositions of Examples 19 and 20 are the same as those of Examples 7 and 8, respectively (see Table 3). Catalyst precursor compositions were calcined by heating at a rate of 0.4° C./min to the calcination temperature of 390° C. in air at a WHSV of 0.5 $hr^{-1}$, steam at a WHSV of 0.16 $hr^{-1}$, and atmospheric pressure. The catalyst was held at this calcination temperature for 4 hours. The effect of calcination conditions was determined as described for Examples 7 and 8. The initial green pellet properties for Examples 19 and 20 are the same as those for Examples 7 and 8, respectively (see Table 4). Properties of the calcined catalysts relative to the respective catalyst precursors are summarized in Table 13.

TABLE 13

| | Lubricant | Calcined Pellet Copper (%) | Calcined Pellet Density Loss (%) | Calcined Pellet Crush Strength Loss (%) | Calcined Pellet Surface Area Loss (%) | Calcined Pellet Total Pore Volume Loss (%) | Calcined Pellet Average Pore Diameter Increase (%) |
|---|---|---|---|---|---|---|---|
| Ex. 19 | graphite | 0.25 | 13.50 | 65.05 | 37.39 | −5.57 | 67.17 |
| Ex. 20 | MgSt | 0.25 | 10.60 | 21.09 | 6.07 | 4.74 | 1.32 |

Examples 21 and 22

The same system and method for calcination was used as described for Examples 7 and 8. Green pellets made with either graphite or magnesium stearate lubricants and 0.4% copper. The compositions of Examples 21 and 22 are the same as those of Examples 9 and 10, respectively (see Table 6). Catalyst precursor pellets were calcined by heating at a rate of 0.4° C./min to the calcination temperature of 390° C. in nitrogen at a WHSV of 0.5 $hr^{-1}$, steam at a WHSV of 0.0 $hr^{-1}$, and atmospheric pressure. The catalyst was held at this calcination temperature for 12 hours. The effect of calcination conditions was determined as described for Examples 7 and 8. The initial green pellet properties for Examples 21 and 22 are the same as those for Examples 9 and 10, respectively (see Table 7). Properties of the calcined catalysts relative to the respective catalyst precursors are summarized in Table 14.

TABLE 14

| | Lubricant | Calcined Pellet Copper (%) | Calcined Pellet Density Loss (%) | Calcined Pellet Crush Strength Loss (%) | Calcined Pellet Surface Area Loss (%) | Calcined Pellet Total Pore Volume Loss (%) | Calcined Pellet Average Pore Diameter Increase (%) |
|---|---|---|---|---|---|---|---|
| Ex. 21 | graphite | 0.40 | 8.97 | 52.79 | 29.59 | 22.83 | 9.07 |
| Ex. 22 | MgSt | 0.40 | 12.08 | 44.16 | −7.40 | −16.22 | 8.14 |

Examples 23 and 24

The same system and method for calcination was used as described for Examples 7 and 8. Green pellets made with either graphite or magnesium stearate lubricants and 0.25% copper. The compositions of Examples 23 and 24 are the same as those of Examples 7 and 8, respectively (see Table 3). Catalyst precursor pellets were calcined by heating at a rate of 2.0° C./min to the calcination temperature of 425° C. in air at a WHSV of 0.2 $hr^{-1}$, steam at a WHSV of 0.16 $hr^{-1}$, and atmospheric pressure. The catalyst was held at this calcination temperature for 4 hours. The effect of calcination conditions was determined as described for Examples 7 and 8. The initial green pellet properties for Examples 23 and 24 are the same as those for Examples 7 and 8, respectively (see Table 4). Properties of the calcined catalysts relative to the respective catalyst precursors are summarized in Table 15.

TABLE 15

| | Lubricant | Calcined Pellet Copper (%) | Calcined Pellet Density Loss (%) | Calcined Pellet Crush Strength Loss (%) | Calcined Pellet Surface Area Loss (%) | Calcined Pellet Total Pore Volume Loss (%) | Calcined Pellet Average Pore Diameter Increase (%) |
|---|---|---|---|---|---|---|---|
| Ex. 23 | graphite | 0.25 | 15.34 | 66.32 | 39.01 | −7.77 | 75.17 |
| Ex. 24 | MgSt | 0.25 | 12.58 | 20.75 | 24.18 | 5.53 | 24.45 |

Examples 25 and 26

The same system and method for calcination was used as described for Examples 7 and 8. Green pellets made with either graphite or magnesium stearate lubricants and 0.4% copper. The compositions of Examples 25 and 26 are the same as those of Examples 9 and 10, respectively (see Table 6). Catalyst precursor pellets were calcined by heating at a rate of 0.4° C./min to the calcination temperature of 390° C. in nitrogen at a WHSV of 0.5 hr$^{-1}$, steam at a WHSV of 0.0 hr$^{-1}$, and atmospheric pressure. The catalyst was held at this calcination temperature for 12 hours. The effect of calcination conditions was determined as described for Examples 7 and 8. The initial green pellet properties for Examples 21 and 22 are the same as those for Examples 9 and 10, respectively (see Table 7). Properties of the calcined catalysts relative to the respective catalyst precursors are summarized in Table 16.

TABLE 16

| | Lubricant | Calcined Pellet Copper (%) | Calcined Pellet Density Loss (%) | Calcined Pellet Crush Strength Loss (%) | Calcined Pellet Surface Area Loss (%) | Calcined Pellet Total Pore Volume Loss (%) | Calcined Pellet Average Pore Diameter Increase (%) |
|---|---|---|---|---|---|---|---|
| Ex. 25 | graphite | 0.40 | 10.26 | 41.90 | 40.81 | 12.77 | 45.28 |
| Ex. 26 | MgSt | 0.40 | 14.77 | 51.10 | 24.45 | −4.32 | 37.98 |

Example 27

In order to perform a regeneration process, calcination and alkylation are needed first to generate coked catalysts. Calcination was performed at the following conditions: nitrogen (N$_2$) WHSV of 0.5 hour$^{-1}$, gas pressure of 172 kilopascals (25 pounds per square inch gauge (psig)), slow ramp up to 400° C. over 22 hours, followed by a fast ramp to 460° C. over two hours. Alkylation was run at the initial conditions of 460° C., total gas WHSV of 2.5 hour$^{-1}$, 1.4 weight percent methanol/phenol in nitrogen, a total gas pressure of 207 kilopascals (30 psig) and the temperature, pressure, and WHSV were modified to keep 2,6-xylenol selectivity between 60 and 65 percent for 200 hours. For each example, the same calcination and alkylation conditions were maintained for each run so regeneration would start with similar amount of coke accumulated on the used catalysts. For each regeneration run, a stainless steel reactor with an outer diameter of 12.7 millimeters (0.5 inch) was loaded with 10 grams of catalyst and 40 grams of quartz chips as diluent. Each reactor was equipped with a back pressure regulator. The feed was prepared with a methanol to phenol molar ratio 4:1 for all runs and pumped into reactors. An infrared-based gas analyzer was used in regeneration mode to monitor the gas flows. Concentration of oxygen, carbon monoxide, and carbon dioxide can be directly read online. For this regeneration, the Example 10 catalyst precursor used 1 weight percent magnesium stearate as the lubricant and 0.4 weight percent copper in the green pellet. The regeneration conditions were a total gas (nitrogen+air) WHSV of 0.5 hour$^{-1}$, 0 weight percent additional steam (i.e., no water added to the feed), a regeneration pressure of 103 kilopascals (15 psig), and a regeneration temperature of 450° C. Oxygen was fed sequentially at inlet weight concentrations of 5%, 10%, 15%, and 21%, and at each concentration the exit gas was monitored. The oxygen concentration was raised from one level to the next when the exit oxygen concentration had increased to one quarter of the inlet oxygen concentration, and/or exit carbon dioxide was less than 1 weight percent. After the final oxygen break-through (when the exit oxygen concentration reached one quarter of 21%, or 5.25%, the regeneration was ended when the bed temperature decreased to 450° C. (Although the reactor was maintained at 450° C., the bed temperature could exceed that temperature during regeneration because of the exothermic reactions occurring in the catalyst bed. Once regeneration was essentially complete, the gas flow through the reactor bed cooled it to the controlled reactor temperature of 450° C.) The catalyst pellet integrity, expressed as percent fines (measured as weight percent of the regenerated catalyst passing through a 40 mesh US sieve with nominal openings of 400 micrometers), was improved by 84% over regenerated Comparative Example 1 catalyst. Specifically, 84% is the difference between 100% fines obtained for the Comparative Example 1 catalyst and 16% fines obtained for the Example 10 catalyst.

Example 28

The Example 7 catalyst precursor used 1 weight percent graphite as the lubricant and had 0.25 weight percent copper in the green pellet. The regeneration conditions were a total gas (nitrogen+air) WHSV of 0.5 hour$^{-1}$, 0.25 weight percent of additional steam, a regeneration pressure of 172 kilopascals (25 psig), and a regeneration temperature of 437.5° C. Except as specified, the regeneration conditions were the same as those described in Example 27. The catalyst pellet integrity for the regenerated Example 7 catalyst was improved by 64% over the regenerated Comparative Example 1 catalyst.

Example 29

Catalyst precursor pellets having the composition shown in Table 17 were subjected to regeneration conditions that included a total gas (nitrogen+air) WHSV of 0.5 hour$^{-1}$, 0 weight percent of additional steam, a regeneration pressure of 241 kilopascals (35 psig), and a regeneration temperature of 425° C. Except as specified, the regeneration conditions were the same as those described in Example 27. The catalyst pellet integrity for the regenerated catalyst of this example was improved by 57% over the regenerated Comparative Example 1 catalyst.

TABLE 17

| Component | Example 29 |
|---|---|
| MgO | 85.9 |
| PEG | 4.3 |
| HPMAS | 4.3 |
| Water | 4.3 |
| Cu(NO$_3$)$_2$·3H$_2$O | 0.3 |
| MgSt | 0.9 |

Example 30

The Example 9 catalyst precursor used 1 weight percent graphite as the lubricant and had 0.4 weight percent copper in the green pellet. The regeneration conditions were a total gas (nitrogen+air) WHSV of 0.5 hour$^{-1}$, 0.5 weight percent of additional steam, a regeneration pressure of 103 kilopascals (15 psig), and a regeneration temperature of 425° C. Except as specified, the regeneration conditions were the same as those described in Example 27. The catalyst pellet integrity for the regenerated catalyst of this example was improved by 47% over the regenerated Comparative Example 1 catalyst.

Example 31

Catalyst precursor pellets having the composition shown in Table 18 were subjected to regeneration conditions that included a total gas (nitrogen+air) WHSV of 0.5 hour$^{-1}$, 0.5 weight percent of additional steam, a regeneration pressure of 241 kilopascals (35 psig), and a regeneration temperature of 450° C. Except as specified, the regeneration conditions were the same as those described in Example 27. The catalyst pellet integrity for the regenerated catalyst of this example was improved by 46% over the regenerated Comparative Example 1 catalyst.

TABLE 18

| Component | Example 31 |
|---|---|
| MgO | 85.9 |
| PEG | 4.3 |
| HPMAS | 4.3 |
| Water | 4.3 |
| Cu(NO$_3$)$_2$·3H$_2$O | 0.3 |
| Graphite | 0.9 |

Example 32

Catalyst precursor pellets having the composition shown in Table 17 were subjected to regeneration conditions that included a total gas (nitrogen+air) WHSV of 0.5 hour$^{-1}$, 0.5 weight percent of additional steam, a regeneration pressure of 103 kilopascals (15 psig), and a regeneration temperature of 425° C. Except as specified, the regeneration conditions were the same as those described in Example 27. The catalyst pellet integrity for the regenerated catalyst of this example was improved by 29% over the regenerated Comparative Example 1 catalyst.

Example 33

Catalyst precursor pellets having the Example 10 composition were subjected to regeneration conditions that included a total gas (nitrogen+air) WHSV of 0.5 hour$^{-1}$, 0.5 weight percent of additional steam, a regeneration pressure of 241 kilopascals (35 psig), and a regeneration temperature of 450° C. Except as specified, the regeneration conditions were the same as those described in Example 27. The catalyst pellet integrity for the regenerated catalyst of this example was improved by 25% over the regenerated Comparative Example 1 catalyst.

Example 34

Phenol alkylation reaction was carried out in a powder reactor. The catalyst precursor had the composition of Example 31, summarized above in Table 18. Catalyst precursor pellets were crushed and sized to particles corresponding to nominal sieve openings of 0.42 to 0.84 millimeters.

A vapor phase reactor having dimensions (height=40 centimeters, and outer diameter=1.27 centimeter) was packed in center with 5 grams of catalyst precursor. The reactor was also packed with glass beads (2 millimeter diameter) supported by thermo wool at the top and bottom layer of catalyst bed. Catalyst particles were packed in the reactor. The effective catalyst bed length was around 9 centimeters. The catalyst calcination was carried out by heating at the rate of 5° C./minute to the calcination temperature of 390° C. under atmospheric pressure nitrogen for 22 hours with a WHSV of 0.11 hour$^{-1}$. After 22 hours, the calcination was complete and the temperature was raised to the reaction temperature of 475° C. at the rate of 0.5° C./minute with a nitrogen flow WHSV of 0.15 hour$^{-1}$. Once the reaction temperature was achieved, the nitrogen flow was stopped and the reaction pressure set to 271 kilopascals (1.7 bar gauge) and maintained constant throughout the reaction. Vapor phase reactants comprising a mole ratio of methanol to phenol equal to 4:1 with 20% water by weight (Phenol:Methanol:water=33:47:20 by weight) were fed at a WHSV of 2.5 hour$^{-1}$ using an HPLC pump. The reaction effluents pass through a condenser followed by a gas-liquid separator where condensed vapors and non-condensable gas (mainly, H$_2$, CO, CH$_4$ and CO$_2$) were separated. Performance parameters from steady-state conditions are reported as the average values between 100 and 170 hrs. For these alkylation conditions, the catalyst performance summary is presented in Table 19, where "Phenol Conv. (%)" is the percent conversion of phenol; "Mesitol Select. (%)" is the percent selectivity for mesitol based on moles of converted phenol; "o-Cresol Select. (%)" is the percent selectivity for ortho-cresol based on moles of converted phenol; "2,6-Xylenol Select. (%)" is the percent selectivity for 2,6-xylenol based on moles of converted phenol; "Cum. Phenol Usage" is the cumulative phenol usage, which is unitless and equal to the quantity of phenol fed to the reactor divided by the quantity of phenol converted in the reactor; "Cum. MeOH Usage" is the cumulative methanol usage, which is unitless and equal to the quantity of methanol fed to the reactor divided by the quantity of methanol converted in the reactor.

TABLE 19

| | Phenol Conv. (%) | Mesitol Select. (%) | o-Cresol Select. (%) | 2,6-Xylenol Select. (%) | Cum. Phenol Usage | Cum. MeOH Usage | Catalyst Activity |
|---|---|---|---|---|---|---|---|
| Ex. 34 | 96.52 | 7.70 | 10.40 | 80.60 | 0.87 | 0.66 | 1.03 |

Example 35

Phenol alkylation was carried out in the system described in Example 34. The catalyst calcination was carried out by heating at the rate of 5° C./min to the calcination temperature of 390° C. under atmospheric nitrogen pressure for 22 hours with a nitrogen WHSV of 0.11 hour$^{-1}$. After 22 hours, the calcination was complete and the temperature was raised to the reaction temperature of 460° C. at a rate of 0.5° C./minute with a nitrogen WHSV of 0.15 hour$^{-1}$. Once the reaction temperature was achieved, nitrogen flow was stopped and the reaction pressure was set to 271 kilopascals (1.7 bar gauge) and maintained constant throughout the reaction. Vapor phase reactants (Phenol:Methanol:water=33:47:20 by weight) were fed at a WHSV of 1.8 hour$^{-1}$. For these alkylation conditions, the catalyst performance is summarized in Table 20.

TABLE 20

| | Phenol Conv. (%) | Mesitol Select. (%) | o-Cresol Select. (%) | 2,6-Xylenol Select. (%) | Cum. Phenol Usage | Cum. MeOH Usage | Catalyst Activity |
|---|---|---|---|---|---|---|---|
| Ex. 35 | 89.02 | 9.19 | 16.53 | 72.10 | 0.89 | 0.69 | 0.74 |

Example 36

Phenol alkylation was carried out in the system described in Example 34. The catalyst calcination was carried out by heating at the rate of 5° C./min to the calcination temperature of 450° C. under atmospheric nitrogen pressure for 22 hours with a nitrogen WHSV of 0.11 hour$^{-1}$. After 22 hours, the calcination was complete and the temperature was raised to the reaction temperature of 475° C. at a rate of 0.5° C./minute with a nitrogen WHSV of 0.15 hour$^{-1}$. Once the reaction temperature was achieved, nitrogen flow was stopped and the reaction pressure was set to 351 kilopascals (2.5 bar gauge) and maintained constant throughout the reaction. Vapor phase reactants (Phenol:Methanol:water=33:47:20 by weight) were fed at a WHSV of 2.5 hour$^{-1}$. For these alkylation conditions, the catalyst performance is summarized in Table 21.

TABLE 21

| | Phenol Conv. (%) | Mesitol Select. (%) | o-Cresol Select. (%) | 2,6-Xylenol Select. (%) | Cum. Phenol Usage | Cum. MeOH Usage | Catalyst Activity |
|---|---|---|---|---|---|---|---|
| Ex. 36 | 89.19 | 7.39 | 30.95 | 59.30 | 0.92 | 0.77 | 0.86 |

Example 37

Phenol alkylation was carried out in the system described in Example 34. The catalyst calcination was carried out by heating at the rate of 5° C./min to the calcination temperature of 450° C. under atmospheric nitrogen pressure for 22 hours with a nitrogen WHSV of 0.11 hour$^{-1}$. After 22 hours, the calcination was complete and the temperature was raised to the reaction temperature of 460° C. at a rate of 0.5° C./minute with a nitrogen WHSV of 0.15 hour$^{-1}$. Once the reaction temperature was achieved, nitrogen flow was stopped and the reaction pressure was set to 351 kilopascals (2.5 bar gauge) and maintained constant throughout the reaction. Vapor phase reactants (Phenol:Methanol:water=33:47:20 by weight) were fed at a WHSV of 1.8 hour$^{-1}$. For these alkylation conditions, the catalyst performance is summarized in Table 22.

TABLE 22

|  | Phenol Conv. (%) | Mesitol Select. (%) | o-Cresol Select. (%) | 2,6-Xylenol Select. (%) | Cum. Phenol Usage | Cum. MeOH Usage | Catalyst Activity |
|---|---|---|---|---|---|---|---|
| Ex. 37 | 66.75 | 5.93 | 34.61 | 57.23 | 0.82 | 0.66 | 0.66 |

Comparative Example 2

A typical comparative reaction production cycle is shown in FIG. 1. The catalyst pre-treatment was conducted in flowing nitrogen at a WHSV of 0.15 hour$^{-1}$ while ramping the temperature from ambient to 390° C. over about 36 hours, and then holding the temperature at 390° C. for 16 hours. The vapor phase alkylation reaction of methanol and phenol started at an initial reaction temperature around 430° C., an initial reaction pressure around 301 kilopascals (2 bar gauge), and a relatively low feed WHSV of around 0.6 hour$^{-1}$. The feed WHSV was increased to a maximum of about 2.5 hour$^{-1}$, and then the temperatures, pressures, and WHSV values were adjusted over the course of the production cycle to maintain a 2,6-xylenol selectivity of about 60-65%. The catalyst was used without regeneration over the 60-70 days of reaction and then discarded because it could not be regenerated without disintegrating.

FIG. 1 is a plot of catalyst activity and 2,6-xylenol production (expressed in units of kilograms 2,6-xylenol per kilograms catalyst per day) as a function of alkylation reaction time (expressed in units of days). Both catalyst activity and corresponding 2,6-xylenol production decline markedly over a period of 67 days due to catalyst deactivation and coking.

Example 38, Comparative Example 3

A single tube pilot scale reactor was used to compare the activity of the Comparative Example 1 catalyst precursor and a catalyst precursor having the composition shown in Table 23.

TABLE 23

| Component | Example 38 |
|---|---|
| MgO | 86.9 |
| PEG | 4.3 |
| HPMAS | 4.3 |
| Water | 4.3 |
| Cu(NO$_3$)$_2$•3H$_2$O | 0.1 |
| Graphite | 0.1 |

The single tube reactor was 3.05 meters (10 feet) long and had an inner diameter of 38 millimeters (1.5 inch). There were four 22.9 centimeter (9 inch) catalyst beds in the single tube reactor. The beds were a combination of the catalyst pellets and 2 millimeter borosilicate glass beads. The ratio of glass beads to catalyst was 4:1 by volume. The beds were separated by 7.6 centimeters (3 inches) of 2 millimeter glass beads. The catalyst precursor was calcined at conditions described in Comparative Example 2. The alkylation followed the procedures described in Comparative Example 2. For Comparative Example 3 using the Comparative Example 1 catalyst, only one alkylation was performed for baseline and comparative purposes. For Example 38 using the Table 23 catalyst precursor, two regenerations were performed followed by two more alkylations at the conditions described for Comparative Example 2. The regeneration procedure comprised two temperature stages with the volume percent oxygen increased during each stage as breakthrough was detected on the oxygen analyzer. The total feed WHSV was 0.15 hour$^{-1}$, which corresponded a blend of air and nitrogen. The feed volume percent oxygen was set by mixing air and nitrogen to obtain the target inlet oxygen volume percent per Table 24.

TABLE 24

| Stage Temperature (° C.) | Volume Percent Oxygen (%) | O$_2$ Breakthrough Target to increase inlet O$_2$ (%) |
|---|---|---|
| 425 | 1 | 0.25 |
| 425 | 2 | 0.5 |
| 425 | 5 | 1.25 |
| 425 | 10 | 2.5 |
| 425 | 15 | 3.75 |
| 450 | 3 | 5.2 |
| 450 | 5 | 1.25 |
| 450 | 10 | 2.5 |
| 450 | 15 | 3.75 |
| 450 | 21 | 5.25 |

Breakthrough was determined when the volume percent oxygen measured by the oxygen analyzer was one quarter of the feed oxygen volume percent. The air and nitrogen feed rates were adjusted to lower the percent oxygen if specific temperature limits were reached on any of the internal thermocouples. These temperature limits were 5 and 10° C. above the stage temperature. When the first temperature limit was reached, the air flow rate was reduced by 20% and the nitrogen flow rate was increased to keep the total feed rate constant. If the second temperature limit was reached, the air flow rate was reduced an additional 20% while the nitrogen feed rate was increased. Once the internal temperature(s) had fallen back below the limits, the air and nitrogen feed rates were reset to the original values. When the oxygen breakthrough target of 5.25% at Stage 2 temperature of 450° C. was achieved, the regeneration was over and the reaction restarted.

Figure 2:
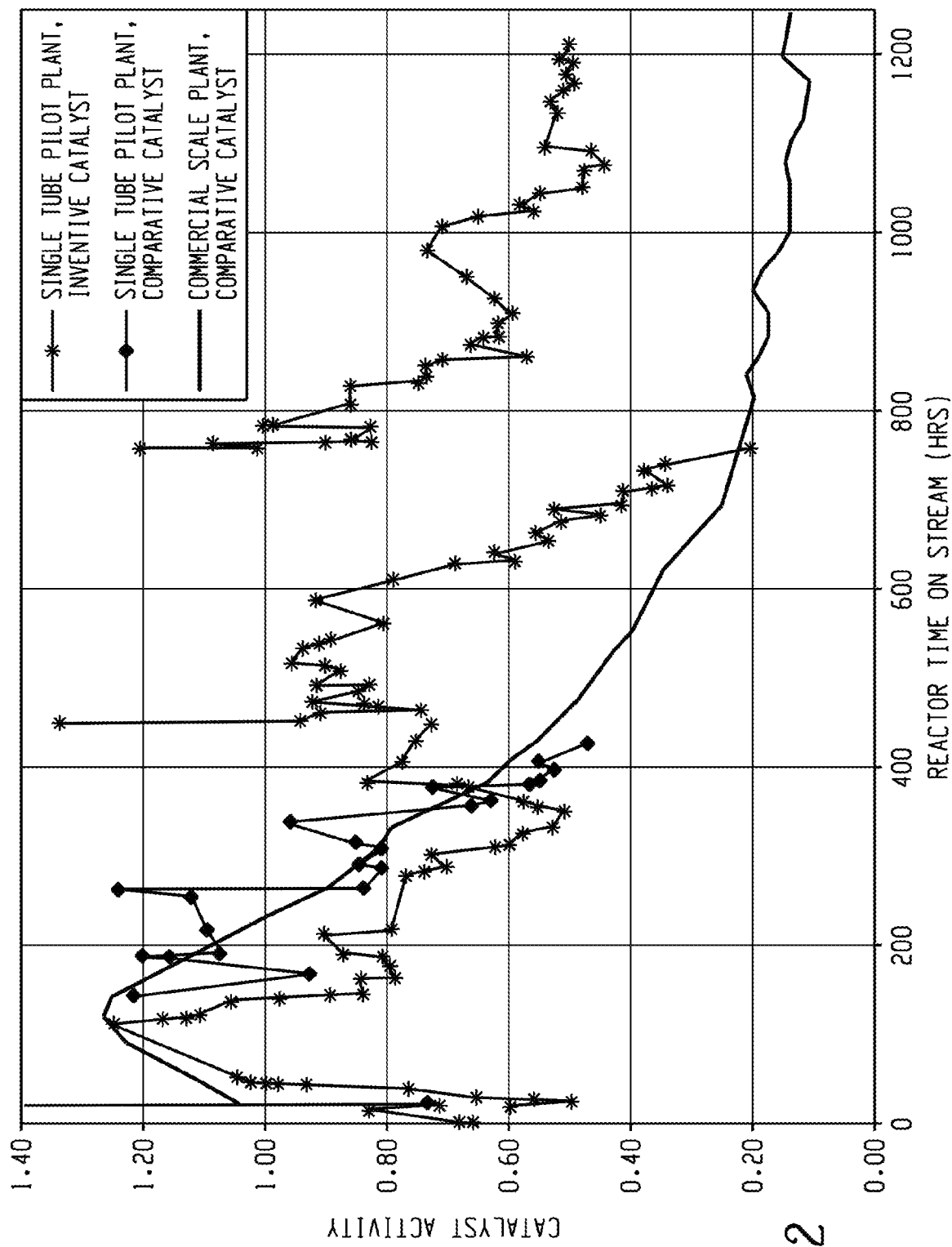
FIG. 2 is a plot of catalyst activity versus time for an inventive catalyst in a single tube pilot reactor ("x"), a comparative catalyst in a single tube pilot reactor ("♦"), and the comparative catalyst in a commercial scale reactor (solid line without data point markers); the inventive catalyst is regenerated twice (at about 460 and 760 hours) during the reaction time studied.

FIG. 2 is a plot of catalyst activity as a function of time, reactor type, and catalyst type. For Example 38, the catalyst was regenerated twice during the test. This example shows how Comparative Example 3 using the Comparative Example 1 catalyst precursor, and Example 38 using the Table 23 catalyst precursor perform in the same pilot reactor at the same reaction conditions. This example shows how the Comparative Example 1 catalyst activity in the pilot reactor is equivalent to its activity in the production-scale multi-tube fixed bed reactor. This example also shows how, by regeneration, the inventive catalyst can operate at higher activities over the same on-stream time and therefore provide increased production of 2,6-xylenol for a given reactor.

Example 39, Comparative Example 4

The catalyst performance was compared on the basis of 2,6-xylenol production as well as activity. The Comparative Example 1 catalyst precursor from Comparative Example 3, above, is compared with the Table 23 catalyst precursor from Example 38.

Figure 3:
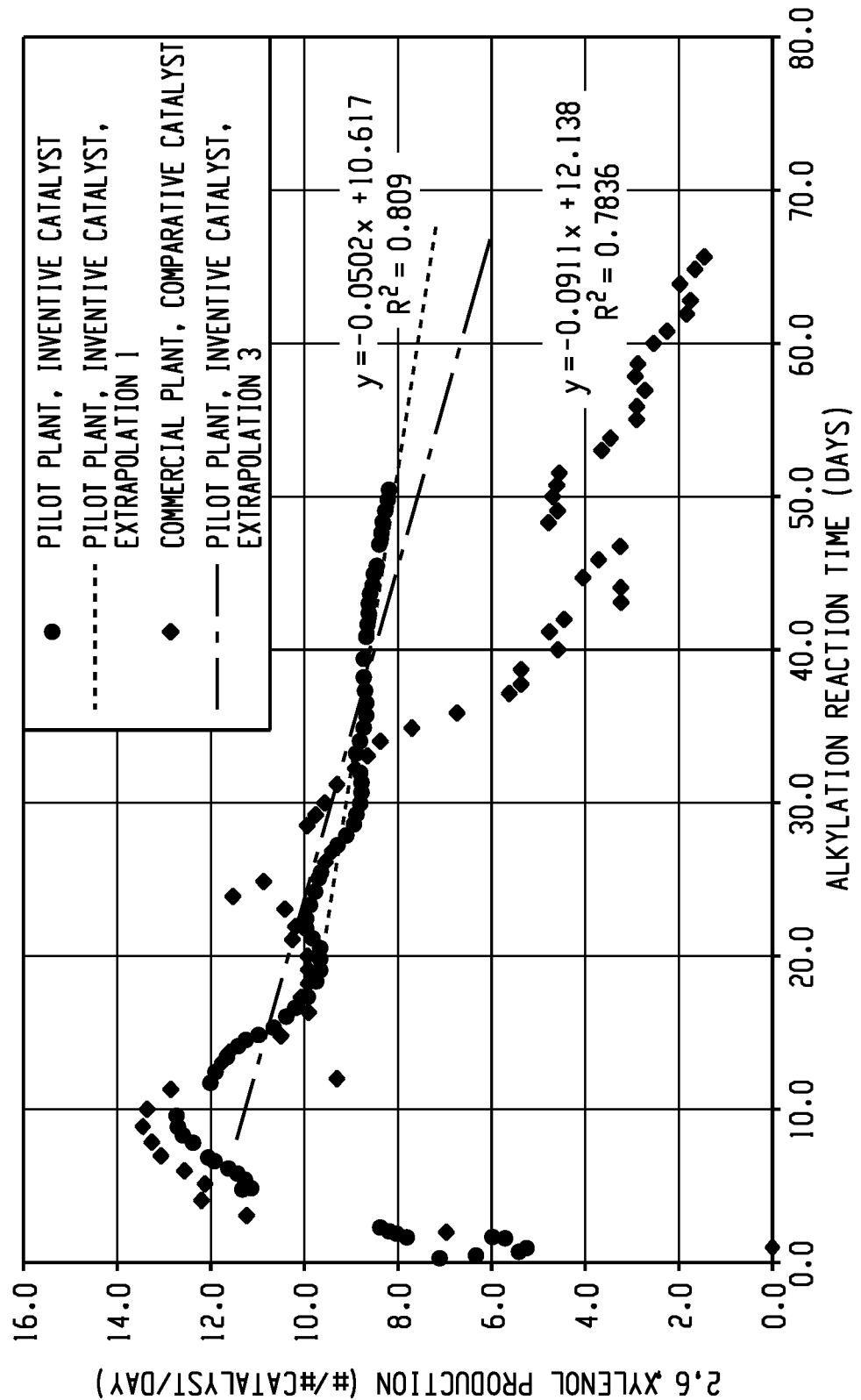
FIG. 3 is a plot of 2,6-xylenol productivity (in kilograms 2,6-xylenol per kilogram catalyst per day) as a function of time for a comparative catalyst in a commercial scale reactor (red diamonds); an inventive catalyst in a pilot scale reactor (blue dots), and two extrapolations of the inventive catalyst curve, with details of the extrapolations explained in the working examples.

FIG. 3 is a plot of 2,6-xylenol production as a function of time, catalyst type, and reactor type. The regression lines were obtained using linear regressions of the data from Example 38 and demonstrate the potential extrapolated production from reduced catalyst deactivation due to regenerability of the catalyst. The first regression estimates the deactivation rate based on days 20 to 50 (after first regeneration, including second regeneration). The second regression estimates the deactivation rate based on days 8 to 50 (all three alkylation cycles and both regenerations, not including initial reaction startup). For Comparative Example 4, the catalyst was not regenerated. For Example 39, the catalyst was regenerated twice during the test. This comparison shows the potential additional 2,6-xylenol production capability of the inventive catalyst with at least 2 regenerations extrapolated over the same reaction period (60-70 days) as the comparative catalyst.

Examples 40-42, Comparative Example 5

Table 25 summarizes catalyst properties as a function of composition, number of regenerations, and alkylation time. In Table 25, "Fresh Catalyst" refers to catalyst precursor, also known as green catalyst; "calcined" refers to catalyst formed by calcining catalyst precursor; "$1^{st}$ Regen." refers to catalyst after a first regeneration; and "Alkylation Time (hours)" is a measure of catalyst lifetime.

TABLE 25

| Catalyst | Property | $1^{st}$ Regen. | $2^{nd}$ Regen. | $3^{rd}$ Regen. | Calcined | Fresh Catalyst | Alkylation Time (hours) |
|---|---|---|---|---|---|---|---|
| C. Ex. 5 | Percent Fines | 100% | N/A | N/A | — | — | 1440 |
| | BET Surface Area ($m^2/g$) | — | — | — | 214 | 62 | — |
| | BET Pore Size (Å) | — | — | — | 94 | 148 | — |
| | BET Pore Volume ($cm^3/g$) | — | — | — | 0.50 | 0.23 | — |
| Ex. 40 | Percent Fines | ~35% | ~65% | ~85% | — | — | 500 |
| | BET Surface Area ($m^2/g$) | 104 | — | 81 | 107 | 103 | — |
| | BET Pore Size (Å) | 115 | — | 184 | 95 | 91 | — |
| | BET Pore Volume ($cm^3/g$) | 0.30 | — | 0.38 | 0.25 | — | — |
| Ex. 41 | Percent Fines | <5% | — | — | — | — | 500 |
| | BET Surface Area ($m^2/g$) | 101 | — | — | 107 | 103 | — |
| | BET Pore Size (Å) | 122 | — | — | 95 | 91 | — |
| | BET Pore Volume ($cm^3/g$) | 0.31 | — | — | 0.25 | — | — |
| Ex. 42 | Percent Fines | — | 0% | — | — | — | 500 |
| | BET Surface Area ($m^2/g$) | — | 144 | — | 132 | 130 | — |
| | BET Pore Size (Å) | — | 87 | — | 89 | 79 | — |
| | BET Pore Volume ($cm^3/g$) | — | 0.31 | — | 0.30 | 0.26 | — |

Examples 43-45

The effect of surface area of the initial MgO used to prepare the catalyst on the alkylation performance of the catalyst was also examined. Catalyst performance was evaluated using a powder reactor, as described above. The physical properties of the initial MgO used to form the catalyst precursors are provided below in Table 26.

TABLE 26

| MgO Sample | SA ($m^2/g$) | Total Pore Vol. (cc/g) | Avg. Pore Diameter (Å) |
|---|---|---|---|
| MgO-1 | 111.7 | 0.77 | 275.6 |
| MgO-2 | 303.5 | 0.54 | 71.28 |
| MgO-3 | 149.8 | 0.60 | 160 |
| MgO-4 | 188.3 | 0.72 | 154 |
| MgO-5 | 74.7 | 1.15 | 617.4 |

Catalysts using the above MgO were prepared having precursor compositions according to Examples 7 and 8, above. For complete formulations of the Example 7 and 8 compositions, see Table 3, where component amounts are expressed in parts by weight. The catalyst pellets were calcined according to the following conditions.

Catalyst using MgO-1 was calcined by heating at a rate of 0.12° C./min to the calcination temperature of 393° C. in air at a weight hourly space velocity (WHSV) of 0.2 $hr^{-1}$, and atmospheric pressure. The MgO was held at this calcination temperature for 15.5 hours.

Catalyst using MgO-2 was calcined by heating at a rate of 0.12° C./min from 393 to 450° C. in nitrogen at a weight hourly space velocity (WHSV) of 0.2 $hr^{-1}$, and atmospheric pressure. The MgO was held at this calcination temperature for 1.5 hours.

Catalyst using MgO-3 was calcined by heating at a rate of 5° C./min to the calcination temperature of 500° C. in air at a weight hourly space velocity (WHSV) of 0.2 $hr^{-1}$, and atmospheric pressure. The MgO was held at this calcination temperature for 10 hours.

Catalyst using MgO-4 was calcined by heating at a rate of 2° C./min to the calcination temperature of 450° C. in nitrogen at a weight hourly space velocity (WHSV) of 0.2 $hr^{-1}$, and atmospheric pressure. The MgO was held at this calcination temperature for 70 hours.

Catalyst using MgO-5 was used as received from ICL Industrial Products.

BET data from the calcined MgO samples is presented in Table 27 below. Each of the samples had 0.25 weight percent copper. Runs were performed in powder reactors with a feed ratio of 4:1 methanol:phenol.

TABLE 27

| Example | MgO Sample | SA (m²/gram) | Total Pore Vol. (cc/g) | Avg. Pore Diameter (Å) |
|---|---|---|---|---|
| 43 | MgO-1 | 94.6 | 0.35 | 147.9 |
| 44 | MgO-4 | 177.7 | 0.45 | 101.6 |
| 45 | MgO-5 | 73.6 | 0.35 | 192.5 |

Each of the catalysts according to Examples 43-45 above were examined for average 2,6-xylenol selectivity, average ortho-selectivity, average phenol conversion, average mesitol selectivity, average activity, and average methanol usage. The results are provided below in Table 28.

TABLE 28

| Example | Avg. 2,6-xylenol selectivity btw TOS of 40-60 hrs | Avg. ortho-selectivity btw TOS of 40-60 hrs | Avg. Phenol Conversion btw TOS of 40-60 hrs (%) | Avg. mesitol selectivity btw TOS of 40-60 hrs (%) | Avg. Activity btw TOS of 40-60 hrs (%) | Avg. methanol usage btw TOS 40-60 hrs |
|---|---|---|---|---|---|---|
| 43 | 54 | 94 | 80 | 4 | 0.82 | 0.69 |
| 44 | 60 | 87 | 98 | 5 | 0.74 | 0.65 |
| 45 | 9 | 94 | 51 | 0.2 | 0.47 | 0.59 |

Figure 4:
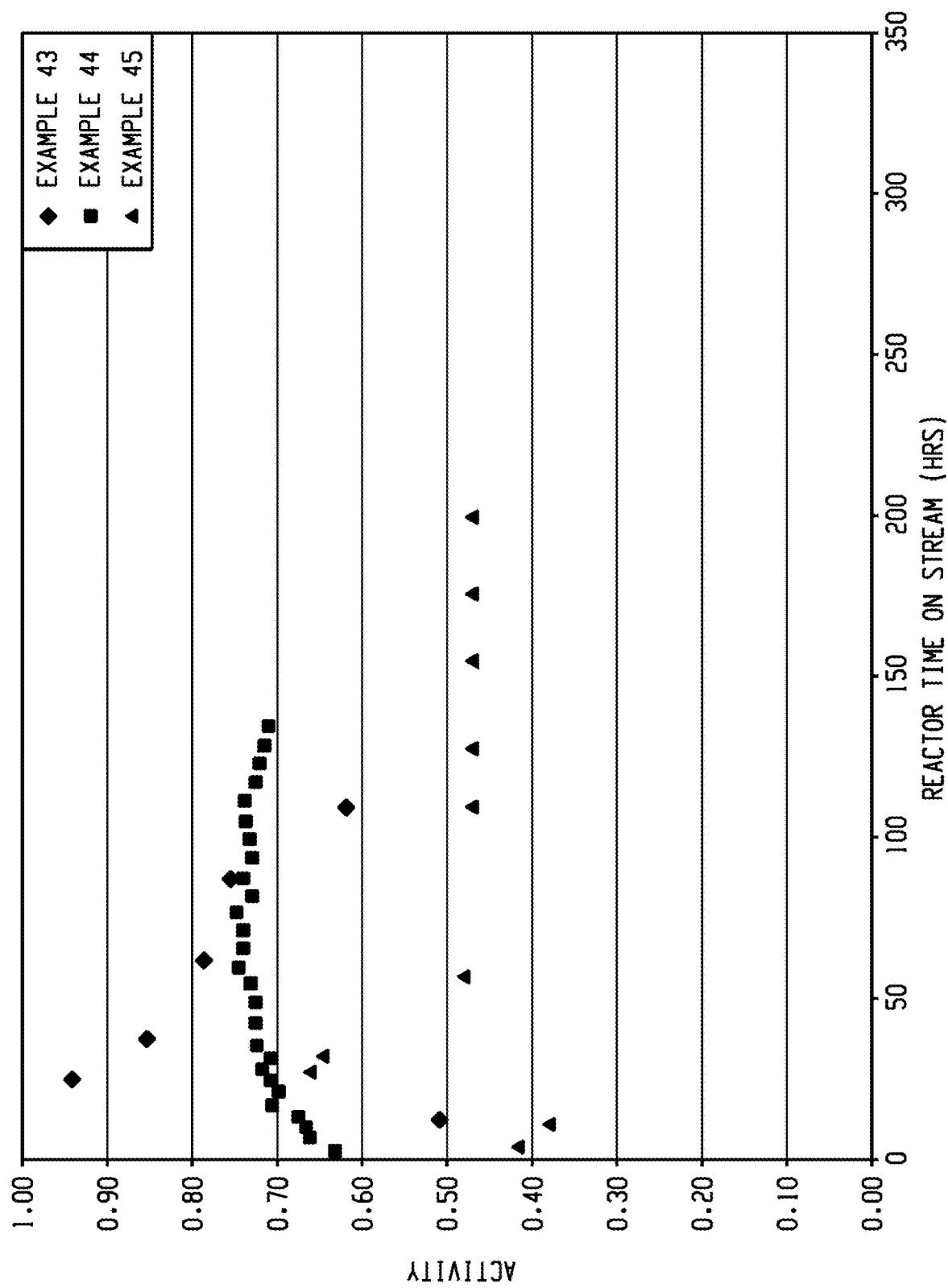
FIG. 4 is a plot of catalyst activity versus time for the catalysts according to example 43 (blue diamonds), example 44 (orange squares), and examples 45 (grey triangles), with details explained in the working examples.
Figure 5:
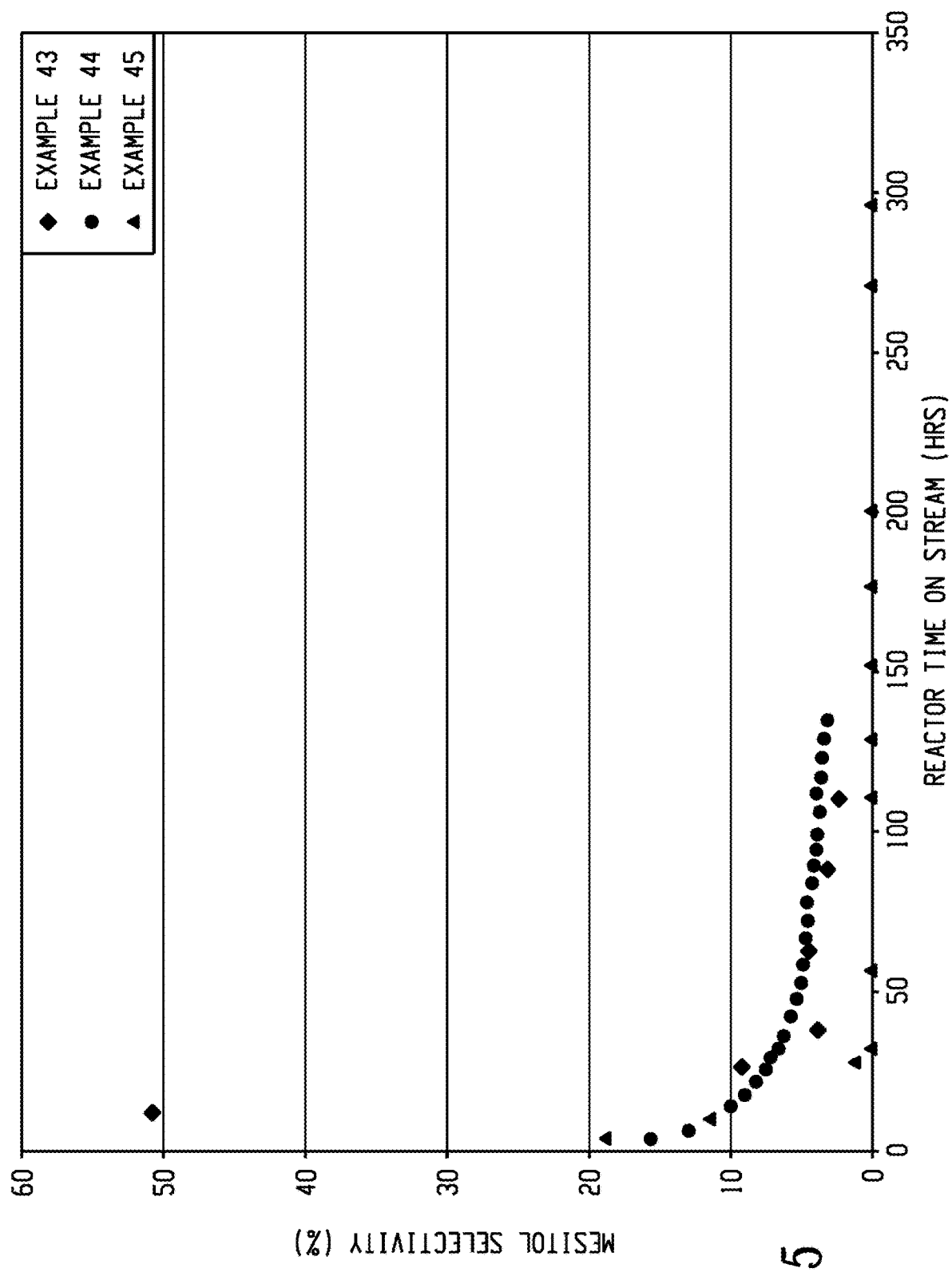
FIG. 5 is a plot of mesitol selectivity (%) versus time for the catalysts according to example 43 (blue diamonds), example 44 (orange squares), and examples 45 (grey triangles), with details explained in the working examples.

As illustrated by the data presented in Table 28, the starting MgO used to prepare the catalyst can result in variation in catalyst performance. Specifically, it can be seen that with a 33% decrease in surface from 111 to 74 m²/g (MgO-1 of example 43 compared to MgO-5 of example 45) results in a 35% decrease in catalyst activity (0.82 to 0.47%). A plot of catalyst activity versus reactor time on stream is shown in FIG. 4. It can also be seen that mesitol selectivity increases with increasing surface area. A plot of mesitol selectivity versus reactor time on stream is shown in FIG. 5.

Accordingly, the data presented herein indicates that the starting MgO having a surface area of 100 to 200 m² per gram can be particularly useful. For example, having a surface area greater than 100 m²/g ensures high catalyst activity, and a surface area of less than 200 m²/g can assist in limiting the amount of mesitol and other impurities in the effluent stream.

The invention claimed is:

1. A catalyst precursor comprising, based on the total weight of the catalyst precursor:
    70 to 98 weight percent of magnesium oxide;
    0.1 to 2 weight percent of copper oxide or a copper oxide precursor;
    0.5 to 8 weight percent of a binder comprising a hydrous magnesium aluminosilicate;
    1 to 15 weight percent of a pore-former;
    0.2 to 5 weight percent of a lubricant; and
    0.2 to 15 weight percent of water;
    wherein the magnesium oxide has a Brunauer-Emmett-Teller surface area of at least 70 meter²/gram.

2. The catalyst precursor of claim 1, having an unpacked density of 1.2 to 2 grams per milliliter at 23° C.

3. The catalyst precursor of claim 1, wherein the copper oxide or a copper oxide precursor comprises cupric oxide, cupric nitrate, cuprous carbonate, a hydrate of one of the foregoing, or a combination thereof.

4. The catalyst precursor of claim 1, wherein the pore-former comprises polyethylene glycol.

5. The catalyst precursor of claim 1, wherein the lubricant comprises graphite, magnesium stearate, or a combination thereof.

6. The catalyst precursor of claim 1, comprising
    75 to 95 weight percent of the magnesium oxide;
    0.2 to 1 weight percent of the copper oxide or copper oxide precursor;
    1 to 6 weight percent of the binder comprising a hydrous magnesium aluminosilicate;
    2 to 10 weight percent of the pore-former;
    0.4 to 3.5 weight percent of the lubricant; and
    0.6 to 12 weight percent of the water.

7. A method of forming a phenol alkylation catalyst, the method comprising:
    exposing the catalyst precursor of claim 1 to a nitrogen gas flow having a weight hourly space velocity of 0.05 to 0.8 hour$^{-1}$, wherein the nitrogen gas flow has a temperature of 350 to 550° C. and is conducted for a time of 5 to 30 hours, and wherein the temperature of the nitrogen gas flow is increased to the temperature of 350 to 550° C. at a rate of 0.5 to 5° C./minute.

8. A phenol alkylation catalyst prepared by a method comprising:
    exposing the catalyst precursor of claim 1 to a nitrogen gas flow having a weight hourly space velocity of 0.05 to 0.8 hour$^{-1}$, wherein the nitrogen gas flow has a temperature of 350 to 550° C. and is conducted for a time of 5 to 30 hours, and wherein the temperature of the nitrogen gas flow is increased to the temperature of 350 to 550° C. at a rate of 0.5 to 5° C./minute;
    wherein the phenol alkylation catalyst exhibits a crush strength of 1 to 20 Newtons/millimeter, determined according to ASTM D4179-11.

9. A method of regenerating the phenol alkylation catalyst of claim 8, the method comprising:
    exposing the phenol alkylation catalyst to a first gas flow having a weight hourly space velocity of 0.05 to 0.8 hour$^{-1}$, a temperature of 410 to 440° C., and a pressure of 25 to 400 kilopascals, wherein the gas flow comprises nitrogen;
    exposing the phenol alkylation catalyst to a second gas flow having a weight hourly space velocity of 0.05 to 0.8 hour$^{-1}$, a temperature of 10 to 50° C. greater than the temperature of the first gas flow, and a pressure of 25 to 400 kilopascals, wherein the gas flow comprises nitrogen.

10. A method of alkylating phenol, the method comprising:
    reacting phenol with a $C_1$-$C_6$ alkanol in the presence of a phenol alkylation catalyst formed by a method comprising:
    exposing the catalyst precursor of claim 1 to a nitrogen gas flow having a weight hourly space velocity of 0.05 to 0.8 hour$^{-1}$, wherein the nitrogen gas flow has a temperature of 350 to 550° C. and is conducted for a time of 5 to 30 hours, and wherein the temperature of the nitrogen gas flow is increased to the temperature of 350 to 550° C. at a rate of 0.5 to 5° C./minute.

11. The method of claim 10, wherein the $C_1$-$C_6$ alkanol comprises methanol, said reacting phenol with a $C_1$-$C_6$ alkanol is characterized by a feed weight hourly space velocity of 0.5 to 10 hour$^{-1}$, a pressure of 50 to 500 kilopascals, a molar ratio of $C_1$-$C_6$ alkanol to phenol of 2:1 to 10:1, and a temperature of 450 to 490° C.

* * * * *